United States Patent
Erickson et al.

(10) Patent No.: US 11,591,633 B2
(45) Date of Patent: Feb. 28, 2023

(54) METHODS AND SYSTEMS FOR THE RAPID DETECTION OF BACTERIA USING RECOMBINANT BACTERIOPHAGE TO EXPRESS AN INDICATOR SUBUNIT

(71) Applicant: Laboratory Corporation of America Holdings, Burlington, NC (US)

(72) Inventors: Stephen E. Erickson, White Bear Township, MN (US); Jose S. Gil, Winnetka, CA (US); Wendy Hahn, Hugo, MN (US); Dwight L. Anderson, Minneapolis, MN (US)

(73) Assignee: Laboratory Corporation of America Holdings, Burlington, NC (US)

(*) Notice: Subject to any disclaimer, the term of this patent is extended or adjusted under 35 U.S.C. 154(b) by 95 days.

(21) Appl. No.: 17/018,693

(22) Filed: Sep. 11, 2020

(65) Prior Publication Data

US 2021/0071225 A1    Mar. 11, 2021

Related U.S. Application Data

(60) Provisional application No. 62/898,945, filed on Sep. 11, 2019.

(51) Int. Cl.
 *C12Q 1/04* (2006.01)
 *C12Q 1/66* (2006.01)

(52) U.S. Cl.
 CPC .............. *C12Q 1/04* (2013.01); *C12Q 1/66* (2013.01); *G01N 2333/005* (2013.01); *G01N 2333/90241* (2013.01)

(58) Field of Classification Search
 None
 See application file for complete search history.

(56) References Cited

U.S. PATENT DOCUMENTS

| | | | |
|---|---|---|---|
| 5,824,468 A | 10/1998 | Scherer et al. | |
| 5,837,465 A | 11/1998 | Squirrel et al. | |
| 6,225,066 B1 | 5/2001 | Jacobs, Jr. et al. | |
| 7,252,996 B2 | 8/2007 | Boccaccio et al. | |
| 8,318,474 B1 | 11/2012 | Smolke et al. | |
| 8,557,970 B2 | 10/2013 | Encell et al. | |
| 8,865,399 B2 | 10/2014 | Schofield et al. | |
| 9,482,668 B2 | 11/2016 | Anderson et al. | |
| 10,519,483 B2 | 12/2019 | Anderson et al. | |
| 2002/0160525 A1 | 6/2002 | Takahata | |
| 2004/0137430 A1 | 7/2004 | Anderson et al. | |
| 2005/0003346 A1 | 1/2005 | Voorhees et al. | |
| 2007/0010001 A1 | 1/2007 | Bujanover | |
| 2009/0155768 A1 | 6/2009 | Scholl et al. | |
| 2009/0246752 A1 | 10/2009 | Voorhees et al. | |
| 2010/0291541 A1 | 11/2010 | Evoy et al. | |
| 2011/0201013 A1 | 8/2011 | Moore | |
| 2011/0281329 A1 | 11/2011 | Lenherr et al. | |
| 2013/0122549 A1 | 5/2013 | Lu et al. | |
| 2013/0216997 A1 | 8/2013 | Anderson et al. | |
| 2015/0218616 A1 | 8/2015 | Anderson et al. | |
| 2017/0121688 A1 | 5/2017 | Gil et al. | |
| 2019/0218590 A1 | 7/2019 | Nguyen et al. | |

FOREIGN PATENT DOCUMENTS

| | | |
|---|---|---|
| CN | 104245961 | 5/2017 |
| EP | 0743366 | 11/1996 |
| JP | 11337553 | 12/1999 |
| JP | 2002-160525 | 6/2002 |
| JP | 2005-524394 | 8/2005 |
| JP | 2006-510002 | 3/2006 |
| JP | 2007-523628 | 8/2007 |
| JP | 2010-507371 | 3/2010 |
| JP | 2010-088456 | 4/2010 |
| JP | 6636967 | 12/2019 |
| WO | 99/45396 | 9/1999 |
| WO | 2003/035889 | 5/2003 |
| WO | 2005/001475 | 1/2005 |
| WO | 2007055737 | 5/2007 |
| WO | 2008/124119 | 10/2008 |
| WO | 2013/126584 | 8/2013 |
| WO | 2015/126966 | 8/2015 |
| WO | 2017/127434 | 7/2017 |

OTHER PUBLICATIONS

Bachrach, U. and Friedman, A., "Practical Procedures for the Purification of Bacterial Viruses," Applied Microbiology, 22(4):706-715 (1971).

Bague, J., "Detection of Recombinant Human Erythropoietin and Analogues through Immunorecognition and N-Giycolyi-Neuraminic Acid Identification," Doctoral Thesis Pompeu Fabra University, Department of Experimental and Health Sciences, 2011, Retrieved from http://www.tesisenred.net/bitstream/handle/10803/31969/tjm.pdf?sequence=1 as available via the Internet and printed Mar. 27, 2013.

Billard, P. and Dubow, M., "Bioluminescence-Based Assays for Detection and Characterization of Bacteria and Chemicals in Clinical Laboratories," Clin. Biochem. 31(1):1-14 (1998).

Edgar, R. et al., "High-sensitivity bacterial detection using biotin-tagged phage and quantum-dot nanocomplexes," Proc. Natl. Acad. Sci. USA, 2006, 103(13):4841-5.

Elena, C. et al., "Expression of codon optimized genes in microbial systems: current industrial applications and perspectives," Frontiers in Microbiol. 5(21):1-8 (2014).

Goodridge, L. et al., "Reporter bacteriophage assays as a means to detect foodborne pathogenic bacteria," Food Research International, 2002, 35:863-870.

Hagens, S. et al., Reporter bacteriophage A511::celB transduces a hyperthermostable glycosidase from Pyrococcus furiosus for rapid and simple detection of viable Listeria cells, Bacteriophage, 2011, 1(3):143-151. Epub May 1, 2011.

(Continued)

Primary Examiner — Nicole Kinsey White
(74) Attorney, Agent, or Firm — Kilpatrick Townsend & Stockton LLP

(57) ABSTRACT

Disclosed herein are methods and systems for rapid detection of microorganisms such as bacteria in a sample. A genetically modified bacteriophage is also disclosed which comprises an indicator gene encoding one subunit of an indicator protein. The specificity of the bacteriophage allows detection of a particular bacteria of interest and an indicator signal may be amplified to optimize assay sensitivity.

7 Claims, 10 Drawing Sheets

(56) References Cited

OTHER PUBLICATIONS

Hagens, S. and Loessner, M., "Bacteriophage for Biocontrol of foodborne pathogens: calculations and considerations," Curr. Pharm. Biotechnol., 2010, 11(1):58-68.
He, Y. et al., "Monoclonal antibodies for detection of the H7 antigen of *Escherichia coli*," Appl. Environ Microbiol., 1996, 62(9):3325-32.
Inouye, S. et al., Overexpression, purification and characterization of the catalytic component of *Oplophorus luciferase* in the deep-sea shrimp, *Oplophorus gracilirostris*, Protein Expr. Purif., 2007, 56(2):261-8.
Jacobs, W., et al., "Rapid Assessment of Drug Susceptibilities of *Mycobacterium tuberculosis* by Means of Luciferase Reporter Phages," Science 260:819-822 (1993).
Kodikara, C. et al., "Near on-line detection of enteric bacteria using lux recombinant bacteriophage," FEMS Microbiol. Lett., 1991, 67(3):261-5.
Kutter, E. et al., "Characterization of a Vil-like Phage Specific to *Escherichia coli* O157:H7," Virology J. 8:430 (2011).
Loessner, M. et al., Construction of Luciferase Reporter Bacteriophage A511::luxAB for Rapid and Sensitive Detection of Viable *Listeria* Cells, Appl. Environ. Microbiol., 1996, 62(4):1133-40.
Loessner, M. et al., "Evaluation of Luciferase Reporter Bacteriophage A511::luxAB for Detection of *Listeria monocytogenes* in Contaminated Foods," Appl. Environ. Microbiol., 1997, 63(8):2961-5.
Lu, T. et al., "Advancing bacteriophage-based microbial diagnostics with synthetic biology," Trends Biotechnol., 2013, 31(6):325-7.
McDonald, P. and Mosig, G., "Regulation of a new bacteriophage T4 gene, 69, that spans an origin of DNA replication," The EMBO J. 3(12):2863-2871 (1984).
Miyanaga, K., et al., "Detection of *Escherichia coli* in the sewage influent by fluorescent labeled T4 phage," Biochem. Engin. J. 29:119-124 (2006).
Noguera, P. et al., "Carbon nanoparticles in lateral flow methods to detect genes encoding virulence factors of Shiga toxin-producing *Escherichia coli*," Anal Bioanal. Chem., 2011, 399(2): 831-838.
Rees, C and Botsaris, G., Chapter 14—The use of phage detection, antibiotic sensitivity testing and enumeration, In: Understanding Tuberculosis—Global Experiences and Innovative Approaches to the Diagnosis, 2012, Intech, Edited by Dr. Pere-Joan Cardona.
Rees, C., "The Use of Phage of Diagnostic Systems," Division of Food Sciences, School of Biosciences, University of Nottingham, Sutton Bonington Campus Loughborough, Leicestershire LE12 5RD, Uk; The Bacteriophages, 2nd edition (2006) Richard Calendar—Oxford University Press, 15 pages.
Schofield, D. et al., "Phage-based platforms for the clinical detection of human bacterial pathogens," Bacteriophage, 2(2):105-283 (2012).
Smietana, M. et al., "Detection of bacteria using bacteriophages as recognition elements immobilized on long-period fiber gratings," Optics Express., 2011, 19(9):7971-8.
Tanji, Y. et al., "*Escherichia coli* Detection by GFP-labeled Lysozyme-inactivated T4 Bacteriophage," J. Biotechnol. 114(1-2):11-20 (2004).
Ulitzur, N. et al., "New rapid and simple methods for detection of bacteria and determination of their antibiotic susceptibility by using phage mutants," Appl. Environ. Microbiol., 2006, 72(12):7455-7459.
Wu, L. et al., "Trace detection of specific viable bacteria using tetracysteine-tagged bacteriophages," Anal Chem. 2014, 86(1):907-12.
Zink, R. and Loessner, M., "Classification of Virulent and Temperate Bacteriophages of *Listeria* spp. on the Basis of Morphology and Protein Analysis," Applied and Environmental Microbiol. 58(1):296-302 (1992).

U.S. Appl. No. 13/773,339, Non-Final Office Action, dated Oct. 31, 2014.
U.S. Appl. No. 13/773,339, Final Office Action, dated Jun. 9, 2015.
U.S. Appl. No. 13/773,339, Non-Final Office Action, dated Mar. 3, 2016, 26 pages.
U.S. Appl. No. 15/263,619, Non-Final Office Action, dated May 13, 2019, 21 pages.
U.S. Appl. No. 15/263,619, Final Office Action, dated Feb. 12, 2020, 27 pages.
U.S. Appl. No. 14/625,481, Non-Final Office Action, dated Jan. 25, 2018, 8 pages.
U.S. Appl. No. 14/625,481, Non-Final Office Action, dated Apr. 26, 2017, 9 pages.
U.S. Appl. No. 14/625,491, Final Office Action, dated Jun. 13, 2019, 11 pages.
U.S. Appl. No. 15/263,619, Non-Final Office Action, dated Mar. 26, 2018, 19 pages.
U.S. Appl. No. 15/409,258, Final Office Action, dated Sep. 17, 2019, 11 pages.
U.S. Appl. No. 15/409,258, Non-Final Office Action, dated Apr. 20, 2020, 6 pages.
AU 2013222411, First Examination Report, dated Nov. 2, 2017, 4 pages.
CA 2,865,308, Office Action, dated Jun. 4, 2018, 3 pages.
CA 2,865,308, Office Action, dated Jun. 4, 2019, 11 pages.
CA 2,865,308, Office Action, dated May 1, 2020, 3 pages.
CN 201380019483, Notification of the First Office Action, dated Jul. 7, 2015.
CN 201380019483, Notification of the Second Office Action, dated Feb. 4, 2016.
CN 201380019483, Notification of the Third Office Action, dated Jul. 18, 2016.
EP 17703002.0, Office Action, dated Dec. 18, 2019, 5 pages.
CN 201710263366.1, Office Action, dated Jul. 31, 2018, 10 pages.
CN 201710263366.1, Office Action, dated Jul. 31, 2019, 10 pages.
EP 13751965, Extended European Search Report, dated Sep. 30, 2015.
EP 13751965.8, Communication Pursuant to Article 94(3) EPC, dated Apr. 11, 2017, 6 pages.
EP 13751965.8, Communication Pursuant to Article 94(3) EPC, dated Jan. 30, 2018, 6 pages.
EP 19152164.0, Extended European Search Report, dated Jul. 10, 2019, 6 pages.
International Patent Application No. PCT/US2017/013955, Search Report, dated May 15, 2017.
International Patent Application No. PCT/US2017/013955, International Preliminary Report on Patentability, dated Aug. 2, 2018, 9 pages.
International Patent Application No. PCT/US2017/013955, Invitation to Pay Additional Fees and Partial Search Report, dated Mar. 20, 2017, 7 pages.
International Application No. PCT/US2015/016415, International Search Report and Written Opinion, dated Jun. 22, 2015.
JP 2014-558827, Office Action, dated Nov. 1, 2016.
JP 2017-016551, Office Action, dated Dec. 21, 2018, 12 pages.
JP 2017-016551, Notice of Reasons for Rejection, dated Jan. 19, 2018, 5 pages.
JP 2017-16551, Notice of Allowance, dated Nov. 20, 2019, 3 pages.
JP 2017-16551, Office Action, dated Sep. 6, 2019, 4 pages.
MX/A/2014/010069, Office Action, dated Apr. 25, 2017, 2 pages.
Dale, N. et al., "NanoBRET: The Bright Future of Proximity-Based Assays," Front. Bioeng. Biotechnol. 7:56 (2019) 13 pages.
England, C. et al., "NanoLuc: A Small Luciferase Is Brightening up the Field of Bioluminescence," Bioconjugate Chem., 27(5):1175-1187 (2016).
PCT/US2020/050490, International Preliminary Report on Patentability, dated Mar. 24, 2022, 7 pages.
PCT/US2020/050490, International Search Report and Written Opinion, dated Nov. 12, 2020, 11 pages.

| Parent Phage | Fusion Protein | HR Donor plasmid | Vector Backbone | GENEWIZ clone ID | Protease Cleavage Site | HR HOST | Strain | Phage Lot |
|---|---|---|---|---|---|---|---|---|
| TSP1 | MCP | TSP1.HR.MCP-PS-HiBit | pUC57-AMP | HB4733-2 | PreScission | S. enterica | 19585 | 100319A-B |
| | MCP | TSP1.HR.MCP-TEV-HiBit | pUC57-AMP | HB4733-4 | Tobacco Etch Virus | S. enterica | 19585 | |
| | MCP | TSP1 HR.HiBit-PS-MCP | pUC57-AMP | HB4733-3 | PreScission | S. enterica | 19585 | |
| | MCP | TSP1 HR.HiBit-TEV-MCP | pUC57-AMP | HB4733-5 | Tobacco Etch Virus | S. enterica | 19585 | |
| | none | TSP1.HR.sol-HiBit | pUC57-AMP | HB4733-1 | None | S. enterica | 19585 | 091819 |
| | none | TSP1.HR.HiBit-HiBit | pUC57-AMP | HB5178-1 | PreScission | S. enterica | 19585 | NA |
| | none | TSP1.HR.HiBit-HiBit-HiBit | pUC57-AMP | HB5178-2 | PreScission | S. enterica | 19585 | 121119 |
| | Aprotinin | TSP1.HR.Aprotinin-HiBit | pUC57-AMP | HB5178-3 | PreScission | S. enterica | 19585 | NA |
| TSP12 | MCP | TSP12.HR.MCP-PS-HiBit | pUC57-AMP | HB4742-5 | PreScission | S. bongori | 43975 | Incomplete |
| | MCP | TSP12.HR.MCP-TEV-HiBit | pUC57-AMP | HB4742-6 | Tobacco Etch Virus | S. bongori | 43975 | Incomplete |
| | none | TSP12.HR.sol-HiBit | pUC57-AMP | HB4742-1 | None | S. bongori | 43975 | 093019 |
| | SOC | TSP12 HR.HiBit-PS-Soc | pUC57-AMP | HB4742-2 | PreScission | S. bongori | 43975 | 112219P |
| | SOC | TSP12 HR.HiBit-TEV-Soc | pUC57-AMP | HB4742-3 | Tobacco Etch Virus | S. bongori | 43975 | 103119 112219T |
| SEA1 | None | SEA1.Sol-HiBit | pUC57-AMP | FB1828-1 | None | S. enterica | 14028 | NA |
| | MCP | SEA1. MCP-PS-HiBit | pUC57-AMP | FB1828-2 | PreScission | S. enterica | 14028 | |
| | MCP | SEA1. MCP-TEV-HiBit | pUC57-AMP | FB1828-3 | Tobacco Etch Virus | S. enterica | 14028 | |
| T7 Select® | MCP | T7Select MCP-3C-HiBit | pUC57-AMP | LB3840-3 | PreScission | E. coli | DH10B | |
| | MCP | T7Select MCP-TEV-HiBit | pUC57-AMP | LB3840-2 | Tobacco Etch Virus | E. coli | DH10B | |
| | none | T7Select 415-SolHiBit | pUC57-AMP | LB3840-1 | None | E. coli | DH10B | 091119 Plaque |

FIG. 4

METHODS AND SYSTEMS FOR THE RAPID DETECTION OF BACTERIA USING RECOMBINANT BACTERIOPHAGE TO EXPRESS AN INDICATOR SUBUNIT

CROSS REFERENCE TO RELATED APPLICATION

The present application claims priority to U.S. Provisional Application No. 62/898,945, filed on Sep. 11, 2019. The disclosures of U.S. application Ser. Nos. 13/773,339, 14/625,481, 15/263,619, and 15/409,258 are incorporated by reference in their entirety herein.

FIELD OF THE INVENTION

This disclosure relates to compositions, methods, systems, and kits for the detection of microorganisms using infectious agents.

BACKGROUND

There is a strong interest in improving speed and sensitivity for detection of bacteria, viruses, and other microorganisms in biological, food, water, and clinical samples. Microbial pathogens can cause substantial morbidity among humans and domestic animals, as well as immense economic loss. Also, detection of microorganisms is a high priority for the Food and Drug Administration (FDA) and Centers for Disease Control (CDC), as well as the United States Department of Agriculture (USDA), given outbreaks of life-threatening or fatal illness caused by ingestion of food contaminated with certain microorganisms, e.g., *Escherichia coli, Cronobacter* spp., *Salmonella* spp., *Listeria* spp., or *Staphylococcus* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving direct immunoassays or gene probes generally require an overnight enrichment step in order to obtain adequate sensitivity. Polymerase chain reaction (PCR) tests also include an amplification step and therefore are capable of both very high sensitivity and selectivity; however, the sample size that can be economically subjected to PCR testing is limited. With dilute bacterial suspensions, most small sub samples will be free of cells and therefore purification and/or lengthy enrichment steps are still required.

The time required for traditional biological enrichment is dictated by the growth rate of the target bacterial population of the sample, by the effect of the sample matrix, and by the required sensitivity. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water, or other product may have already made its way into livestock or humans. In addition, increases in antibiotic-resistant bacteria and biodefense considerations make rapid identification of bacterial pathogens in water, food and clinical samples critical priorities worldwide.

Therefore, there is a need for more rapid, simple, and sensitive detection and identification of microorganisms, such as bacteria and other potentially pathogenic microorganisms.

SUMMARY

Embodiments of the disclosure comprise compositions, methods, systems, and kits for the detection of microorganisms such as. The disclosure may be embodied in a variety of ways.

In some aspects, the disclosure comprises a recombinant indicator bacteriophage comprising an indicator gene inserted into the bacteriophage genome, wherein the indicator gene encodes a peptide subunit of an indicator protein (indicator protein product). In certain embodiments the indicator bacteriophage comprises a genetically modified bacteriophage genome derived from a bacteriophage that specifically recognizes a particular bacteria of interest.

In some embodiments of the recombinant indicator bacteriophage, the peptide subunit (labeling subunit) is part of a split reporter enzyme system, wherein the reporter enzyme (i.e., indicator protein) is a luciferase. The luciferase can be naturally occurring, such as Oplophorus luciferase, Firefly luciferase, Lucia luciferase, or *Renilla* luciferase, or it can be a genetically engineered luciferase such as NANOLUC®.

Also disclosed herein are methods for preparing an indicator bacteriophage. Some embodiments include selecting a wild-type bacteriophage that specifically infects a target pathogenic bacterium; preparing a homologous recombination plasmid/vector comprising an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage.

In another aspect, the disclosure comprises a method for detecting a particular bacteria of interest in a sample comprising the steps of incubating the sample with a recombinant indicator bacteriophage comprising an indicator gene, wherein the indicator gene encodes a first subunit of an indicator protein, thereby producing an amount of progeny phage and expressing the first subunit; lysing the bacteria in the sample to release the amount of progeny phage and the first subunit; incubating the lysed sample in the presence of a detection reagent, wherein the detection reagent comprises a second subunit of an indicator protein, thereby allowing the first subunit and second subunit to reconstitute to form an indicator protein complex; and detecting the indicator protein complex, wherein positive detection of the indicator protein complex indicates that the particular bacteria of interest is present in the sample.

In some embodiments of methods for detecting bacteria, the sample is first incubated in conditions favoring growth for an enrichment period of 24 hours or less, 23 hours or less, 22 hours or less, 21 hours or less, 20 hours or less, 19 hours or less, 18 hours or less, 17 hours or less, 16 hours or less, 15 hours or less, 14 hours or less, 13 hours or less, 12 hours or less, 11 hours or less, 10 hours or less, or 9 hours or less, 8 hours or less, 7 hours or less, 6 hours or less, 5 hours or less, 4 hours or less, 3 hours or less, or 2 hours or less. In some embodiments, the sample is not enriched prior to detection. In some embodiments, the total time to results is less than 26 hours, 25 hours, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours or 2 hours. In some embodiments, the ratio of signal to background generated by detecting the indicator is at least 2.0 or at least 2.5 or at least 3.0. In some embodiments, the method detects as few as 1, 2, 3, 4, 5, 6, 7, 8, 9, 10, 15, 20, 30, 40, 50, 60, 70, 80, 90, or 100 of the specific bacteria in a sample of a standard size for the food safety industry.

Additional embodiments include systems and kits for detecting particular bacteria of interest, wherein the systems or kits include an indicator bacteriophage derived from bacteriophage specific for the particular bacteria of interest. These systems or kits can include features described for the bacteriophage, compositions, and methods of the disclosure. In still other embodiments, the disclosure comprises non-transient computer readable media for use with methods or systems according to the disclosure.

BRIEF DESCRIPTION OF THE FIGURES

The present disclosure may be better understood by referring to the following non-limiting figures.

FIG. 4 provides a table detailing homologous recombination constructs made using parental phage: TSP1, TSP12, SEA1, and T7 Select according to an embodiment of the disclosure.

DETAILED DESCRIPTION OF THE DISCLOSURE

Figure 1:
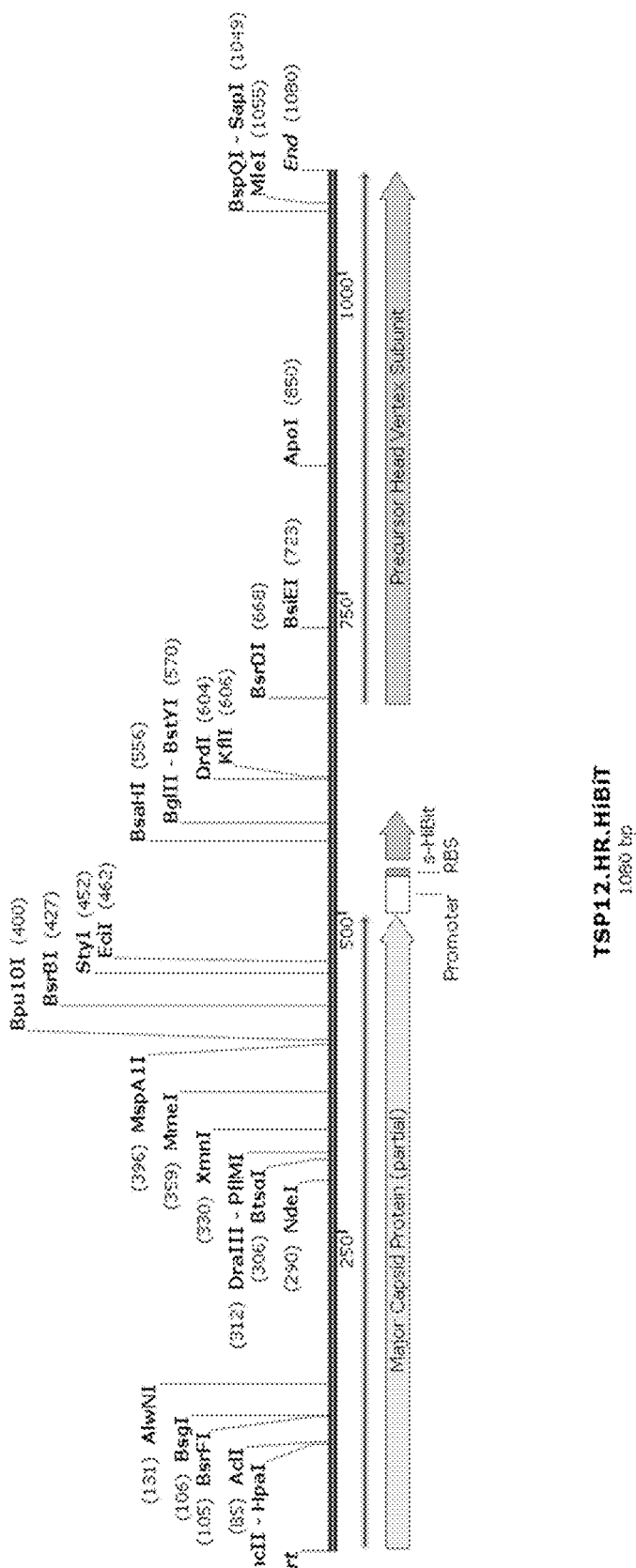
FIG. 1 depicts an indicator phage construct according to an embodiment of the disclosure illustrating the insertion of a genetic construct comprising a promoter, RBS, and indicator gene (soluble HiBiT) inserted into a TSP12 bacteriophage downstream of the major capsid protein.

Disclosed herein are compositions, methods and systems that demonstrate surprising sensitivity for detection of a microorganism of interest, such as *Escherichia coli, Cronobacter* spp., *Salmonella* spp *Listeria* spp., or *Staphylococcus* spp., in test samples (e.g., biological, food, water, and environmental). Detection can be achieved in a shorter timeframe than was previously thought possible using genetically modified infectious agents in assays performed without culturing for enrichment, or in some embodiments with minimal incubation times during which microorganisms could potentially multiply. Also surprising is the success of using a potentially high multiplicity of infection (MOI), or high concentrations of plaque forming units (PFU), for incubation with a test sample. Such high phage concentrations (PFU/mL) were previously purported to be detrimental in bacterium detection assays, as they were purported to cause "lysis from without." However, a high concentration of phage can facilitate finding, binding, and infecting a low number of target cells.

The compositions, methods, systems and kits of the disclosure may comprise infectious agents for use in detection of microorganisms such as *Escherichia coli, Cronobacter* spp., *Salmonella* spp., *Listeria* spp., or *Staphylococcus* spp. a recombinant indicator bacteriophage comprising an indicator gene inserted into the bacteriophage genome, wherein the indicator gene encodes a peptide subunit of an indicator protein. In certain embodiments, expression of the indicator gene during bacteriophage replication following infection of a host bacterium results in production of a soluble peptide subunit of an indicator protein. In alternative embodiments, of a fused peptide subunit of an indicator protein. In certain embodiments, the indicator gene may be inserted into a late gene (i.e., class III) region of the bacteriophage.

In some embodiments, the disclosure comprises a method for detecting a particular bacteria of interest in a sample comprising the steps of incubating the sample with a recombinant indicator bacteriophage comprising an indicator gene, wherein the indicator gene encodes a first subunit of an indicator protein, thereby producing an amount of progeny phage expressing the first subunit; lysing the amount of progeny phage; incubating the lysed progeny phage in the presence of a detection reagent, wherein the detection reagent comprises a second subunit of an indicator protein, thereby allowing the first subunit and second subunit to reconstitute to form an indicator protein complex; and detecting the indicator protein complex, wherein positive detection of the indicator protein complex indicates that the particular bacteria of interest is present in the sample.

In certain embodiments, the disclosure may comprise a system. The system may contain at least some of the compositions of the disclosure. Also, the system may comprise at least some of the components for performing the method. In certain embodiments, the system is formulated as a kit. Thus, in certain embodiments, the disclosure may comprise a system for rapid detection of a particular bacteria of interest in a sample, comprising: a component for incubating the sample with an infectious agent specific for the microorganism of interest, wherein the infectious agent comprises an indicator moiety; and a component for detecting the indicator moiety. In yet other embodiments, the disclosure comprises software for use with the methods or systems.

Thus, some embodiments of the present disclosure solve a need by using bacteriophage-based methods for amplifying a detectable signal indicating the presence of bacteria. In certain embodiments as little as a single bacterium is detected. The principles applied herein can be applied to the detection of a variety of microorganisms. Because of numerous binding sites for an infectious agent on the surface of a microorganism, the capacity to produce one hundred or more agent progeny during infection, and the potential for high level expression of an encoded indicator moiety, the infectious agent or an indicator moiety can be more readily detectable than the microorganism itself. In this way, embodiments of the present disclosure can achieve tremendous signal amplification from even a single infected cell.

Aspects of the present disclosure utilize the high specificity of binding agents that can bind to particular microorganisms, such as the binding component of infectious agents, as a means to detect and/or quantify the specific microorganism in a sample. In some embodiments, the present disclosure utilizes the high specificity of infectious agents such as bacteriophage.

In some embodiments, detection is achieved through an indicator moiety associated with the binding agent specific for the microorganism of interest. For example, an infectious agent may comprise a gene encoding an indicator protein or a subunit thereof. In some embodiments the indicator may be encoded by the infectious agent, such as a bacteriophage, and the bacteriophage is designated an indicator phage.

Some embodiments of the disclosure disclosed and described herein utilize the discovery that a single microorganism is capable of binding specific recognition agents, such as phage. Following infection and replication of the phage, progeny phage may be detected via an indicator gene expressed during phage replication. This principle allows amplification of indicator signal from one or a few cells based on specific recognition of microorganism surface receptors. For example, by exposing even a single cell of a bacterium to a plurality of phage, thereafter allowing amplification of the phage and high-level expression of an encoded indicator gene product, or subunit of an indicator protein, during replication, the indicator signal is amplified such that the single bacterium is detectable.

Embodiments of the methods and systems of the disclosure can be applied to detection and quantification of a variety of microorganisms (e.g., bacteria) in a variety of circumstances, including but not limited to detection of pathogens from food, water, and commercial samples. The methods of the present disclosure provide high detection sensitivity and specificity rapidly. In some embodiments detection is possible within a single replication cycle of the bacteriophage, which is unexpected.

Definitions

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

As used herein, "solid support" or "support" means a structure that provides a substrate and/or surface onto which biomolecules may be bound. For example, a solid support may be an assay well (i.e., such as a microtiter plate or multi-well plate), or the solid support may be a location on a filter, an array, or a mobile support, such as a bead or a membrane (e.g., a filter plate, latex particles, paramagnetic particles, or lateral flow strip).

As used herein, "binding agent" refers to a molecule that can specifically and selectively bind to a second (i.e., different) molecule of interest. The interaction may be non-covalent, for example, as a result of hydrogen bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, the term "bioluminescence" refers to production and emission of light by a chemical reaction catalyzed by, or enabled by, an enzyme, protein, protein complex, or other biomolecule (e.g., bioluminescent complex). In typical embodiments, a substrate for a bioluminescent entity (e.g., bioluminescent protein or bioluminescent complex) is converted into an unstable form by the bioluminescent entity; the substrate subsequently emits light.

As used herein the term "complementary" refers to the characteristic of two or more structural elements (e.g., peptide, polypeptide, nucleic acid, small molecule, etc.) of being able to hybridize, dimerize, or otherwise form a complex with each other. For example, a "complementary peptide and polypeptide" are capable of coming together to form a complex. Complementary elements may require assistance to form a complex (e.g., from interaction elements), for example, to place the elements in the proper conformation for complementarity, to co-localize complementary elements, to lower interaction energy for complementary, etc.

As used herein, the term "complex" refers to an assemblage or aggregate of molecules (e.g., peptides, polypeptides, etc.) in direct and/or indirect contact with one another. In one aspect, "contact," or more particularly, "direct contact" means two or more molecules are close enough so that attractive non-covalent interactions, such as Van der Waal forces, hydrogen bonding, ionic and hydrophobic interactions, and the like, dominate the interaction of the molecules. In such an aspect, a complex of molecules (e.g., a peptide and polypeptide) is formed under assay conditions such that the complex is thermodynamically favored (e.g., compared to a non-aggregated, or non-complexed, state of its component molecules). As used herein the term "complex," unless described as otherwise, refers to the assemblage of two or more molecules (e.g., peptides, polypeptides or a combination thereof).

As used herein, the term "non-luminescent" refers to an entity (e.g., peptide, polypeptide, complex, protein, etc.) that exhibits the characteristic of not emitting a detectable amount of light in the visible spectrum (e.g., in the presence of a substrate). For example, an entity may be referred to as non-luminescent if it does not exhibit detectable luminescence in a given assay. As used herein, the term "non-luminescent" is synonymous with the term "substantially non-luminescent. For example, a non-luminescent polypeptide is substantially non-luminescent, exhibiting, for example, a 10-fold or more (e.g., 100-fold, 200-fold, 500-fold, $1 \times 10^3$-fold, $1 \times 10^4$-fold, $1 \times 10^5$-fold, $1 \times 10^6$-fold, $1 \times 10^7$-fold, etc.) reduction in luminescence compared to a complex of the NLpoly with its non-luminescent complement peptide. In some embodiments, an entity is "non-luminescent" if any light emission is sufficiently minimal so as not to create interfering background for a particular assay.

As used herein, the terms "non-luminescent peptide" and "non-luminescent polypeptide" refer to peptides and polypeptides that exhibit substantially no luminescence (e.g., in the presence of a substrate), or an amount that is beneath the noise, or a 10-fold or more (e.g., 100-fold, 200-fold, 500-fold, $1 \times 10^3$-fold, $1 \times 10^4$-fold, $1 \times 10^5$-fold, $1 \times 10^6$-fold, $1 \times 10^7$-fold, etc.) when compared to a significant signal (e.g., luminescent complex) under standard conditions (e.g., physiological conditions, assay conditions, etc.) and with typical instrumentation (e.g., luminometer, etc.). In some embodiments, such non-luminescent peptides and polypeptides assemble, according to the criteria described herein, to form a bioluminescent complex. As used herein, a "non-luminescent element" is a non-luminescent peptide or non-luminescent polypeptide. The term "bioluminescent complex" refers to the assembled complex of two or more non-luminescent peptides and/or non-luminescent polypeptides. The bioluminescent complex catalyzes or enables the conversion of a substrate for the bioluminescent complex into an unstable form; the substrate subsequently emits light. When uncomplexed, two non-luminescent elements that form a bioluminescent complex may be referred to as a "non-luminescent pair." If a bioluminescent complex is formed by three or more non-luminescent peptides and/or non-luminescent polypeptides, the uncomplexed constituents of the bioluminescent complex may be referred to as a "non-luminescent group."

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

As used herein, "detectable moiety" or "detectable biomolecule" or "reporter" or "indicator" or "indicator protein" or "indicator protein product" "indicator protein complex" or "indicator moiety" refers to a molecule that can be measured in a quantitative assay. For example, an indicator protein may comprise an enzyme that may be used to convert a substrate to a product that can be measured. An indicator moiety may be an enzyme that catalyzes a reaction that generates bioluminescent emissions (e.g., luciferase). Or, an indicator moiety may be a radioisotope that can be quantified. Or, an indicator moiety may be a fluorophore. Or, other detectable molecules may be used.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less. Bacteriophages are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, "late gene region" refers to a region of a viral genome that is transcribed late in the viral life cycle. The late gene region typically includes the most abundantly expressed genes (e.g., structural proteins assembled into the bacteriophage particle). Late genes are synonymous with class III genes and include genes with structure and assembly functions. For example, the late genes (synonymous with class III) are transcribed in phage T7, e.g., from 8 minutes after infection until lysis, class I (e.g., RNA polymerase) is early from 4-8 minutes, and class II from 6-15 minutes, so there is overlap in timing of II and III. A late promoter is one that is naturally located and active in such a late gene region.

As used herein, "culturing for enrichment" refers to traditional culturing, such as incubation in media favorable to propagation of microorganisms, and should not be confused with other possible uses of the word "enrichment," such as enrichment by removing the liquid component of a sample to concentrate the microorganism contained therein, or other forms of enrichment that do not include traditional facilitation of microorganism propagation. Culturing for enrichment for periods of time may be employed in some embodiments of methods described herein.

As used herein "recombinant" refers to genetic (i.e., nucleic acid) modifications as usually performed in a laboratory to bring together genetic material that would not otherwise be found. This term is used interchangeably with the term "modified" herein.

As used herein "RLU" refers to relative light units as measured by a luminometer (e.g., GLOMAX® 96) or similar instrument that detects light. For example, the detection of the reaction between luciferase and appropriate substrate (e.g., NANOLUC® with NANO-GLO®) is often reported in RLU detected.

As used herein "time to results" refers to the total amount of time from beginning of sample incubation to generated result. Time to results does not include any confirmatory testing time. Data collection can be done at any time after a result has been generated.

As used herein "reporter gene" or "indicator gene" may refer to a complete gene or to a portion of a gene. For example, the use of indicator gene or reporter gene herein may include a nucleotide sequence that encodes a smaller peptide subunit, i.e., that is transcribed and translated into a partial protein.

Samples

Each of the embodiments of the methods and systems of the disclosure can allow for the rapid detection and quantification of microbes in a sample. For example, methods according to the present disclosure can be performed in a shortened time period with superior results.

Microbes detected by the methods and systems of the present invention include pathogens that are of natural, commercial, medical or veterinary concern. Such pathogens include Gram-negative bacteria, Gram-positive bacteria, and mycoplasmas. Any microbe for which an infectious agent that is specific for the particular microbe has been identified can be detected by the methods of the present invention. Those skilled in the art will appreciate that there is no limit to the application of the present methods other than the availability of the necessary specific infectious agent/microbe pairs.

Bacterial cells detectable by the present disclosure include, but are not limited to, bacterial cells that are food or water borne pathogens. Bacterial cells detectable by the present invention include, but are not limited to, all species of *Salmonella*, all strains of *Escherichia coli, Cronobacter, Staphylococcus*, all species of *Listeria*, including, but not limited to *L. monocytogenes*, and all species of *Campylobacter*. Bacterial cells detectable by the present invention include, but are not limited to, bacterial cells that are pathogens of medical or veterinary significance. Such pathogens include, but are not limited to, *Bacillus* spp., *Bordetella pertussis, Campylobacter jejuni, Chlamydia pneumoniae, Clostridium perfringens, Enterobacter* spp., *Klebsiella pneumoniae, Mycoplasma pneumoniae, Salmonella typhi, Shigella sonnei, Staphylococcus aureus*, and *Streptococcus* spp. In some embodiments, bacterial cells detectable by the present invention include antibiotic-resistant bacteria (e.g., methicillin-resistant *Staphylococcus aureus* (MRSA).

The sample may be an environmental or food or water sample. Some embodiments may include medical or veterinary samples. Samples may be liquid, solid, or semi-solid. Samples may be swabs of solid surfaces. Samples may include environmental materials, such as the water samples, or the filters from air samples or aerosol samples from cyclone collectors. Samples may be of vegetables, meat, fish, poultry, peanut butter, processed foods, powdered infant formula, powdered milk, teas, starches, eggs, milk, cheese, or other dairy products. Medical or veterinary samples include, but are not limited to, blood, sputum, cerebrospinal fluid, and fecal samples and different types of swabs.

In some embodiments, samples may be used directly in the detection methods of the present disclosure, without preparation, concentration, or dilution. For example, liquid samples, including but not limited to, milk and juices, may be assayed directly. Samples may be diluted or suspended in a solution, which may include, but is not limited to, a buffered solution or a bacterial culture medium. A sample that is a solid or semi-solid may be suspended in a liquid by mincing, mixing or macerating the solid in the liquid. A sample should be maintained within a pH range that promotes bacteriophage attachment to the host bacterial cell. A sample should also contain the appropriate concentrations of divalent and monovalent cations, including but not limited to $Na^+$, $Mg^{2+}$, and $Ca^{2+}$. Preferably, a sample is maintained at a temperature that supports the viability of any pathogen cells contained within the sample.

Preferably throughout detection assays, the sample is maintained at a temperature that maintains the viability of any pathogen cell present in the sample. During steps in which bacteriophages are attaching to bacterial cells, it is preferable to maintain the sample at a temperature that facilitates bacteriophage attachment. During steps in which bacteriophages are replicating within an infected bacterial cell or lysing such an infected cell, it is preferable to maintain the sample at a temperature that promotes bacteriophage replication and lysis of the host. Such temperatures are at least about 25 degrees Celsius (C), more preferably no greater than about 45 degrees C., most preferably about 37 degrees C.

Assays may include various appropriate control samples. For example, control samples containing no bacteriophages or control samples containing bacteriophages without bacteria may be assayed as controls for background signal levels.

Indicator Bacteriophage

As described in more detail herein, the compositions, methods, systems and kits of the invention may comprise infectious agents for use in detection of pathogenic microorganisms. In certain embodiments, the present disclosure comprises a recombinant indicator bacteriophage, wherein the bacteriophage genome is genetically modified to include an indicator or reporter gene. In some embodiments, the invention may include a composition comprising a recombinant bacteriophage having an indicator gene incorporated into the genome of the bacteriophage, wherein the indicator gene encodes a peptide subunit of an indicator protein.

A recombinant indicator bacteriophage can include a reporter or indicator gene or an indicator peptide subunit. In some embodiments of the indicator bacteriophage, the indicator or peptide subunit gene encodes a fusion protein. For example, the indicator or indicator peptide subunit may be fused with a bacteriophage capsid protein, such that the indicator is expressed as part of the bacteriophage capsid. The indicator may also be fused with another protein for production as a soluble molecule. In other embodiments of the indicator bacteriophage, the indicator gene does not encode a fusion protein. For example, in certain embodiments, expression of the indicator gene during bacteriophage replication following infection of a host bacterium results in a non-fusion soluble indicator protein product. In certain embodiments, the indicator or indicator peptide or polypeptide subunit gene may be inserted into a late gene region of the bacteriophage. Late genes are generally expressed at higher levels than other phage genes, as they code for structural proteins. The late gene region may be a class III gene region and may include a gene for a major capsid protein.

Some embodiments include designing (and optionally preparing) a sequence for homologous recombination downstream of the major capsid protein gene. Other embodiments include designing (and optionally preparing) a sequence for homologous recombination upstream of the major capsid protein gene. In some embodiments, the sequence comprises a codon-optimized reporter gene preceded by an untranslated region. The untranslated region may include a phage late gene promoter and ribosomal entry site.

In some embodiments, an indicator bacteriophage is derived from the selected wild-type bacteriophage *Salmonella* phage SPN1S, *Salmonella* phage 10, *Salmonella* phage epsilon15, *Salmonella* phage SEA1, *Salmonella* phage TSP1, *Salmonella* phage TSP12, *Salmonella* phage Spn1s, *Salmonella* phage P22, *Listeria* phage LipZ5, *Listeria* phage P40, *Listeria* phage vB_LmoM_AG20, *Listeria* phage P70, *Listeria* phage A511, *Listeria* phage P100, *Listeria* phage LMA8, *Listeria* phage LMA4, *Staphylococcus* phage P4 W, *Staphylococcus* phage K, *Staphylococcus* phage Twort, *Staphylococcus* phage SA97, *Escherichia coli* O157:H7 phage CBA120, or another bacteriophage having a genome with at least 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% homology to the selected wild-type bacteriophage *Salmonella* phage SPN1S, *Salmonella* phage 10, *Salmonella* phage epsilon15, *Salmonella* phage SEA1, *Salmonella* phage TSP1, *Salmonella* phage TSP12, *Salmonella* phage Spn1s, *Salmonella* phage P22, *Listeria* phage LipZ5, *Listeria* phage P40, *Listeria* phage vB_LmoM_AG20, *Listeria* phage P70, *Listeria* phage A511, *Staphylococcus* phage P4 W, *Staphylococcus* phage K, *Staphylococcus* phage Twort, *Staphylococcus* phage SA97, or *Escherichia coli* 0157:H7 phage CBA120. In some embodiments, the indicator phage is derived from a bacteriophage that is highly specific for a particular pathogenic microorganism. The genetic modifications may avoid deletions of wild-type genes and thus the modified phage may remain more similar to the wild-type infectious agent than many commercially available phage. Environmentally derived bacteriophage may be more specific for bacteria that are found in the environment and as such, genetically distinct from phage available commercially.

In some embodiments, the recombinant bacteriophage comprises a binding domain having ≥95% homology to the binding domain of any of the following bacteriophages: *Salmonella* phage SPN1S, *Salmonella* phage 10, *Salmonella* phage epsilon15, *Salmonella* phage SEA1, *Salmonella* phage TSP1, *Salmonella* phage TSP12, *Salmonella* phage Spn1s, *Salmonella* phage P22, *Listeria* phage LipZ5, *Listeria* phage P40, *Listeria* phage vB_LmoM_AG20, *Listeria* phage P70, *Listeria* phage A511, *Staphylococcus* phage P4 W, *Staphylococcus* phage K, *Staphylococcus* phage Twort, *Staphylococcus* phage SA97, or *Escherichia coli* 0157:H7 phage CBA120.

In certain instances, the indicator phage is derived from a bacteriophage that is highly specific for a particular pathogenic microorganism. In some embodiments the indicator phage is derived from T7Select. T7Select is a commercially available phage display system from Novagen. T7 is a well characterized prototypical phage infecting *Escherichia* from the Podoviridae family. The capsid of T7 phage is comprised of 9:1 ratio of the 2 isoforms of MCP (gp10a and gp10b). The gp10a and gp10b arise from a frame shift in translation and this shift can be modulated to yield different ratios of the gp10a:gp10b isoforms. T7Select® is a cloning plasmid containing the entire T7 genome. A peptide or protein of a certain length can be cloned into the C-terminus of the gp10b and expressed in high (415) medium (5-10) or low (up to 1) copy number per bacteriophage.

In some embodiments, the indicator phage is derived from TSP12, a *Salmonella* phage specific to *Salmonella bongori* strains. This phage is most closely related to Enterobacteria RB51 Phage which belongs to the Tequatrovirus genus. This genus includes the well characterized and studied *Escherichia* T4 virus. This phage has a number of capsid structures published detailing protein components and conformations. TSP12 has several structural candidate genes for tagging with a peptide or polypeptide labeling subunit, including but not limited to the Major Capsid Protein (gp23) and accessory small outer capsid protein (gpSoc).

In some embodiments, the indicator phage is derived from, SEA1, a *Salmonella* phage. SEA1 is most closely related to *Salmonella* phage vB_SenM-516 of the genus Gelderlandvirus [GenBank: HQ331142.1]. SEA1 has several structural candidate genes for tagging with a peptide or polypeptide labeling subunit, including but not limited to the major capsid protein, head vertex protein, head outer capsid protein and small outer capsid protein. The major capsid protein can be tagged on either the amino(N) or carboxy (C) termini.

In some embodiments, the indicator phage is derived from TSP1, a *Salmonella* phage. TSP1 is most closely related to the *Salmonella* and *Escherichia* Kuttervirus genus of phage. The TSP1 phage has at least one candidate gene for tagging with a peptide or polypeptide labeling subunit, including but not limited to, a single major prohead protein.

The genetic modifications may avoid deletions of wild-type genes and thus the modified phage may remain more similar to the wild-type infectious agent than many commercially available phage. Environmentally derived bacteriophage may be more specific for bacteria that are found in the environment and as such, genetically distinct from phage available commercially.

Moreover, phage genes thought to be nonessential may have unrecognized function. For example, an apparently nonessential gene may have an important function in elevating burst size such as subtle cutting, fitting, or trimming functions in assembly. Therefore, deleting genes to insert an indicator may be detrimental. Most phages can package a DNA that is up to ten percent larger than their natural genome. Different viruses, including phages, have varying burst sizes. Burst sizes are heavily dependent on the host, multiplicity of infection (MOI), and growth conditions. Phage lambda and other phages (such as T4, T5 and T7) have burst sizes of about 100-300. In some embodiments, the selected bacteriophage has a burst size of at least 25, 50, 75, 100, 125, 150, 175, 200, 225, 250, 275, 300, 325, 250, 375, 400, 425, 450, 475, or 500 PFU/cell. For example, T7 has a burst size of 180 PFU/cell; T4 has a burst size of 130 PFU/cell; and CBA120 has a burst size of 440 PFU/cell. A smaller burst size means less progeny phage are available for production of an indicator protein product. Thus, the use of a phage with a larger burst size is advantageous in amplifying the signal and increasing assay sensitivity.

Small phage pack smaller genomes, and therefore, have less tolerance for additional transgenes. Another possible advantage to a small reporter gene is that it may be expressed at higher numbers, as each copy of the protein requires fewer finite cellular resources. Yet, the HiBiT tag alone may be too small to be properly expressed, or properly fold.

With these considerations, a smaller indicator gene may be a more appropriate choice for modifying a bacteriophage, especially a bacteriophage with a smaller genome. OpLuc and NANOLUC® proteins are only about 20 kDa (approximately 500-600 bp to encode), while FLuc is about 62 kDa (approximately 1,700 bp to encode). For comparison, the genome of T7 is around 40 kbp, while the T4 genome is about 170 kbp. In some embodiments, the indicator gene encodes a subunit of a reporter protein (e.g., NANOLUC®). In some embodiments, the use of a smaller indicator gene (e.g., a subunit of indicator protein) allows for multiple copies of the indicator gene to be inserted into the phage genome, thereby further amplifying the signal.

Protein complementation assays (PCA) provide a means to detect the interaction of two biomolecules, e.g., polypeptide subunits. PCAs may utilize two subunits of the same protein, e.g., enzyme, that when brought into close proximity with each other can reconstitute into a functional, active protein. PCAs involve the use of at least two subunits of a protein to detect a protein of interest. Thus, in some embodiments of the recombinant indicator bacteriophage, the indicator gene encodes one subunit of a split reporter protein. In certain instances, the split reporter protein is a functional enzyme (e.g., a luciferase or a β-galactosidase). In further embodiments, the luciferase is NANOLUC®. In some embodiments, the split reporter (indicator protein) comprises a first polypeptide subunit (labeling subunit) and a second polypeptide subunit (detection subunit). In still further embodiments, the labeling subunit is complementary to the detection subunit. In certain instances, the labeling subunit is capable of binding the detection subunit to form an indicator protein complex. Thus, in some embodiments of the recombinant indicator bacteriophage, an indicator gene inserted into the bacteriophage genome, wherein the indicator gene encodes a polypeptide subunit (labeling subunit) of an indicator protein.

In certain embodiments of the indicator phage, a gene encoding the labeling subunit is inserted into the phage genome. In further embodiments, the indicator gene during bacteriophage replication following infection of the bacterium of interest results in production of an indicator protein product allowing for protein-protein interactions with a second subunit (detection subunit). In some embodiments, the labeling subunit encounters the detection subunit to form a functional enzyme (e.g., luciferase). In further embodiments, the functional enzyme generates a signal. In some instances, generation of a signal requires the functional enzyme contacts a substrate.

FIG. 1 depicts a schematic representation of the genomic structure of one embodiment of a recombinant bacteriophage of the disclosure, Indicator Phage TSP12.s.HiBiT. For the embodiment depicted in FIG. 1, the indicator protein is encoded by a soluble HiBiT gene inserted within the late (class III) gene region, which is expressed late in the viral life cycle. Late genes are generally expressed at higher levels than other phage genes, as they code for structural proteins. Thus, in the embodiment of the recombinant phage depicted by FIG. 1, the indicator gene (i.e., soluble HiBiT) is inserted into the late gene region, just after the major capsid protein (MCP) gene, and is a construct comprising the HiBiT luciferase gene. Also as depicted by FIG. 1, the construct may comprise a late promoter to drive transcription and expression of the HiBiT gene. The construct may also comprise a composite untranslated region synthesized from several UTRs and stop codons in all 3 reading frames to ensure HiBiT is not incorporated into the MCP gene product. This construct ensures soluble HiBiT is produced such that expression is not limited to the number of capsid proteins inherent in the phage display system.

Figure 2:
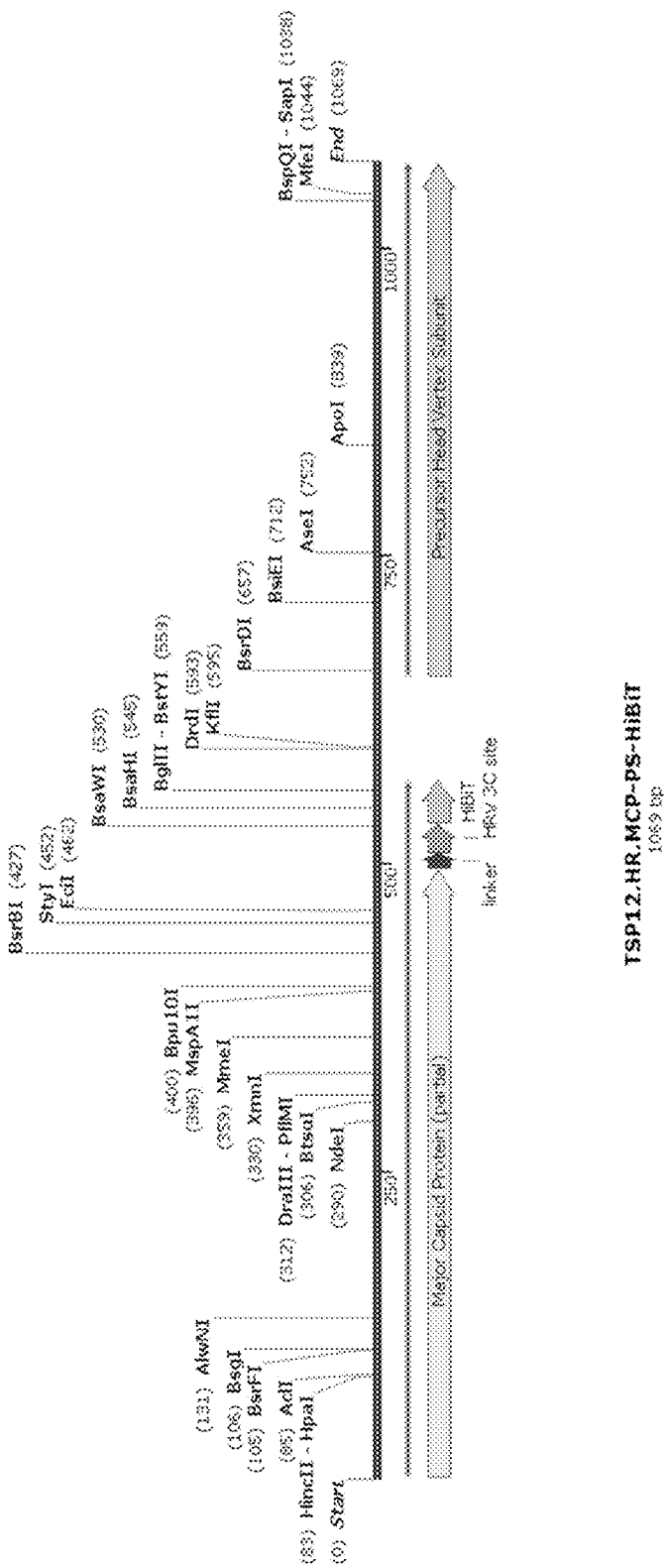
FIG. 2 depicts an indicator phage construct according to an embodiment of the disclosure illustrating the insertion of a genetic construct comprising a linker, HRV 3C site, and indicator gene (HiBiT) inserted into a TSP12 bacteriophage downstream of the major capsid protein.
Figure 3:
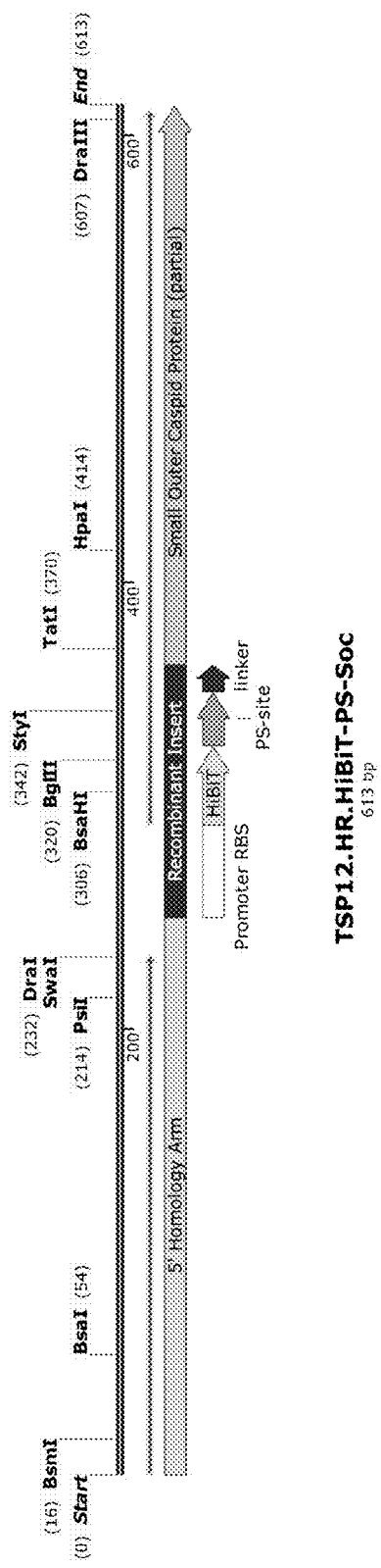
FIG. 3 depicts an indicator phage construct according to an embodiment of the disclosure illustrating the insertion of a genetic construct comprising a linker, PS protease site, and indicator gene (HiBiT) inserted into a TSP12 bacteriophage on the N-terminus of the Soc protein.

FIG. 2 depicts a schematic representation of the genomic structure of a recombinant bacteriophage of the disclosure, Indicator Phage TSP12.MCP-PS-HiBiT. For the embodiment depicted in FIG. 2, a HiBiT gene is inserted at the C-terminus of the MCP to generate a MCP-HiBiT fusion protein. The MCP is located within the late (class III) gene region, which is expressed late in the viral life cycle. Late genes are generally expressed at higher levels than other phage genes, as they code for structural proteins. Thus, in the embodiment of the recombinant phage depicted by FIG. 2, the indicator gene (i.e., HiBiT) is inserted into the late gene region, at the C-terminus of the MCP gene, and is a construct comprising the HiBiT luciferase gene. Also as depicted by FIG. 2, the construct may comprise a linker and HRV 3C protease cut site. The HRV 3C protease cut site allows for HiBit to be removed from the phage during phage preparation.

In some embodiments, the NANO-GLO® HiBiT Detection System (Promega Corporation) may be used to detect molecular proximity by virtue of the reconstitution of a luminescent enzyme via the binding interaction of enzyme components or subunits. The NANO-GLO® HiBiT Detection System utilizes a peptide tag (HiBiT) and a polypeptide (LgBiT) derived from the Oplophorus luciferase variant, NANOLUC®. In some embodiments, HiBiT (11 amino acids) is the labeling subunit and LgBiT (156 amino acids) is the detection subunit. Thus, in some embodiments, the indicator phage comprises an indicator gene, wherein the indicator gene is HiBiT. When the HiBiT peptide encounters the LgBiT peptide, they reconstitute to form a full-length, functional luciferase enzyme. In some embodiments, the detection reagent comprises the complementing polypeptide, LgBiT, which spontaneously interacts with the HiBiT tag to reconstitute a bright, luminescent enzyme. enzyme. In some embodiments, the indicator protein complex is combined with Promega's NANO-GLO®, an imidazopyrazinone substrate (furimazine), can provide a robust signal with low background. In some embodiments, the detection reagent comprises NANO-GLO®.

In some embodiments, the detection subunit has a high affinity for the labeling subunit. In further embodiments, the labeling subunit is capable of binding to the detection subunit to from an indicator complex. HiBiT binds tightly to LgBiT, thus, promoting formation of a luciferase indicator complex. In some embodiments, the binding affinity (equilibrium dissociation constant ($K_D$)) between the labeling subunit and the detection subunit is at least 0.2, 0.3, 0.4, 0.5, 0.6, 0.7, 0.8, 0.9, or 1.0 nM.

In some embodiments, each subunit exhibits little to no reporter activity. In certain embodiments, the labeling subunit and the detection subunit are non-luminescent or substantially non-luminescent. In other embodiments, the labeling subunit is luminescent. Moreover, the reporter gene should not be expressed endogenously by the bacteria (i.e., is not part of the bacterial genome), should generate a high signal to background ratio, and should be readily detectable in a timely manner.

In some embodiments, the gene encoding the labeling subunit is inserted into an indicator bacteriophage genome. In certain embodiments, the labeling subunit forms a fusion protein with a phage structural protein. These proteins are the most abundant proteins made by the phage, as each bacteriophage particle comprises dozens or hundreds of copies of these molecules. In some embodiments, the labeling subunit is fused to a phage capsid protein. In other embodiments, the labeling subunit is fused to a phage tail fiber protein. In certain embodiments, the gene encoding the labeling subunit is inserted into a late gene region of the bacteriophage. The late gene region may be a class III gene region and may include a gene for a major capsid protein. In some embodiments, the labeling subunit forms a fusion protein with a capsid protein. For example, the labeling subunit may be fused to the major capsid protein. The major capsid protein is present in multiple copies on the bacteriophage. For example, T4 phage have approximately 1,000 copies of the major capsid protein, thus allowing for further amplification of the signal.

Reporter systems can be problematic in that they can impact proteins with which they interact. In some embodiments, the reporter system has minimal steric burden on its fusion partners. In further embodiments, the reporter system has minimal influence on the affinity and association kinetics of the interacting target proteins. In some embodiments, each subunit has been structurally optimized. In certain embodiments, the labeling subunit is small, so that steric conflicts on fusion partners are minimized. In some instances, the detection subunit is optimized for stability. In some embodiments, it is advantageous for the labeling subunit to be smaller than the detection subunit. Thus, in certain embodiments the labeling subunit is less than 50, 40, 30, 20, 15, 10, or 5 amino acids long. In further embodiments, the detection subunit is at least 50, 60, 70, 80, 90, 100, 110, 120, 130, 140, 150, 160, 170, 180, 190, 200, 210, 220, 230, 240, or 250 amino acids long.

Genetic modifications to infectious agents may include insertions, deletions, or substitutions of a small fragment of nucleic acid, a substantial part of a gene, or an entire gene. In some embodiments, inserted or substituted nucleic acids comprise non-native sequences. A non-native indicator gene may be inserted into a bacteriophage genome such that it is under the control of a bacteriophage promoter. Thus, in some embodiments, the non-native indicator gene is not part of a fusion protein. That is, in some embodiments, a genetic modification may be configured such that the indicator protein product does not comprise polypeptides of the wild-type bacteriophage. In some embodiments, the indicator protein product is soluble. In some embodiments, the disclosure comprises a method for detecting a bacterium of interest comprising the step of incubating a test sample with such a recombinant bacteriophage.

In some embodiments, expression of the indicator gene in progeny bacteriophage following infection of host bacteria results in a free, soluble protein product. In some embodiments, the non-native indicator gene is not contiguous with a gene encoding a structural phage protein and therefore does not yield a fusion protein. In certain instances, it is advantageous to employ a non-fusion protein system. For example, a fusion protein would require the indicator peptide first be cleaved off proteolytically, prior to purification of the phage particles from the peptide tag (e.g., HiBiT) in the stock lysate. Unlike systems that employ a fusion of an indicator protein to the capsid protein (i.e., a fusion protein), some embodiments of the present invention express a soluble indicator or reporter (e.g., soluble luciferase). In some embodiments, the indicator or reporter is ideally free of the bacteriophage structure. That is, the indicator or reporter is not attached to the phage structure. As such, the gene for the indicator or reporter is not fused with other genes in the recombinant phage genome. This may greatly increase the sensitivity of the assay (down to a single bacterium), and simplifies the assay, allowing the assay to be completed in less than an hour for some embodiments, as opposed to several hours due to additional purification steps required with constructs that produce detectable fusion proteins. Further, fusion proteins may be less active than soluble proteins due, e.g., to protein folding constraints that may alter the conformation of the enzyme active site or access to the substrate.

In other embodiments, the fused protein comprising a labeling unit is expressed in progeny bacteriophage following infection of host bacteria. In certain instances, the labeling subunit gene is contiguous with a gene encoding a structural phage protein and therefore yields a fusion protein. Fusion proteins may result in folding constraints that may alter the conformation of the enzyme active site or access to the substrate.

In order to keep the advantages of a non-fusion protein system, and keep the transgene insert small, in some embodiments, the peptide or polypeptide tag (e.g., HiBiT) is fused to a small protein, which may act as a stabilization domain. This can be accomplished by fusing the peptide tag (e.g., HiBiT) to truncated versions of known larger proteins, or fusing the peptide tag (e.g., HiBiT) to known small proteins. For example, small proteins include the 6.5 kDa aprotinin (encoded by 177 nucleotides) or the 14 kDa alpha lactalbumin (encoded by 372 nucleotides). In certain embodiments, a short amino acid linker is present between the domains. Even with the linker region (e.g., HiBiT with a gly-ser-gly-ser linker is 48 nucleotides long), these soluble fusion protein genes would be smaller than other luminescent proteins known in the art (e.g., the 516 nucleotide long NANOLUC®). In some embodiments, the indicator phage encodes a subunit of a reporter, such as a detectable enzyme. The reporter (indicator complex) may generate light and/or may be detectable by a color change. Various appropriate enzymes are commercially available, such as alkaline phosphatase (AP), horseradish peroxidase (HRP), or luciferase (Luc). In some embodiments, these enzymes may serve as the reporter. In some embodiments, Firefly luciferase is the reporter. In some embodiments, Oplophorus luciferase is the reporter. Other engineered luciferases or other enzymes that generate detectable signals may also be appropriate indicator protein products.

In some embodiments, the use of a soluble indicator protein product eliminates the need to remove contaminating parental phage from the lysate of the infected sample cells. With a fusion protein system, any bacteriophage used to infect sample cells would have the indicator protein product attached, and would be indistinguishable from the daughter bacteriophage also containing the indicator protein product. As detection of sample bacteria relies on the detection of a newly created (de novo synthesized) indicator protein product, using fusion constructs requires additional steps to separate old (parental) moieties (indicator proteins) from newly created (daughter bacteriophage) moieties (indicator proteins). This may be accomplished by washing the infected cells multiple times, prior to the completion of the bacteriophage life cycle, inactivating excess parental phage after infection by physical or chemical means, and/or chemically modifying the parental bacteriophage with a binding moiety (such as biotin), which can then be bound and separated (such as by streptavidin-coated sepharose beads). However, even with all these attempts at removal, parental phage can remain when a high concentration of parental phage is used to assure infection of a low number of sample cells, creating background signal that may obscure detection of signal from infected cell progeny phage.

By contrast, with the soluble indicator protein products expressed in some embodiments of the present disclosure, purification of the parental phage from the final lysate is unnecessary, as the parental phage do not have any indicator protein product attached. Thus any indicator protein product present after infection must have been created de novo, indicating the presence of an infected bacterium or bacteria. To take advantage of this benefit, the production and preparation of parental phage may include purification of the phage from any free indicator protein produced during the production of parental bacteriophage in bacterial culture. Standard bacteriophage purification techniques may be employed to purify some embodiments of phage according to the present invention, such as sucrose density gradient centrifugation, cesium chloride isopycnic density gradient centrifugation, HPLC, size exclusion chromatography, and dialysis or derived technologies (such as Amicon brand concentrators—Millipore, Inc.). Cesium chloride isopycnic ultracentrifugation can be employed as part of the preparation of recombinant phage of the invention, to separate parental phage particles from contaminating luciferase protein produced upon propagation of the phage in the bacterial host. In this way, the parental recombinant bacteriophage of the invention is substantially free of any luciferase generated during production in the bacteria. Removal of residual luciferase present in the phage stock can substantially reduce background signal observed when the recombinant bacteriophage are incubated with a test sample.

Standard bacteriophage purification techniques may be employed to purify some embodiments of phage according to the present disclosure, such as sucrose density gradient centrifugation, cesium chloride isopycnic density gradient centrifugation, HPLC, size exclusion chromatography, and dialysis or derived technologies (such as Amicon brand concentrators—Millipore, Inc.). Cesium chloride isopycnic ultracentrifugation can be employed as part of the preparation of recombinant phage of the disclosure, to separate parental phage particles from contaminating luciferase protein produced upon propagation of the phage in the bacterial host. In this way, the parental recombinant bacteriophage of the disclosure is substantially free of any luciferase generated during production in the bacteria. Removal of residual luciferase present in the phage stock can substantially reduce background signal observed when the recombinant bacteriophage are incubated with a test sample.

In some embodiments, the late promoter is a T7, T4, T4-like, Phage K, MP131, MP115, MP112, MP506, MP87, Rambo, SAPJV1 promoter, or another phage promoter similar to that found in the selected wild-type phage, i.e., without genetic modification. The late gene region may be a class III gene region, and the bacteriophage may be derived from T7, T4, T4-like, Phage K, MP131, MP115, MP112, MP506, MP87, Rambo, SAPJV1, Staphylococcus-, or S. aureus-specific bacteriophage, or another natural bacteriophage having a genome with at least 70, 75, 80, 85, 90 or 95% homology to T7, T4, T4-like, Phage K, MP131, MP115, MP112, MP506, MP87, Rambo, SAPJV1, Staphylococcus-, or S. aureus-specific bacteriophage or has high affinity for RNA polymerase of the same bacteriophage that transcribes genes for structural proteins assembled into the bacteriophage particle. The use of a viral late promoter can ensure optimally high level of expression of the luciferase indicator protein product. The use of a late viral promoter derived from, specific to, or active under the original wild-type bacteriophage the indicator phage is derived from (e.g., a T4, T7, ViI, or Saka late promoter with a T4-, T7-, ViI-, or Saka-based system) can further ensure optimal expression of the indicator protein product. The use of a standard bacterial (non-viral/non-bacteriophage) promoter may in some cases be detrimental to expression, as these promoters are often down-regulated during bacteriophage infection (in order for the bacteriophage to prioritize the bacterial resources for phage protein production). Thus, in some embodiments, the phage is preferably engineered to encode and express at high level a soluble (free) indicator protein, using a placement in the genome that does not limit expression to the number of subunits of a phage structural component.

Compositions of the disclosure may comprise one or more wild-type or genetically modified infectious agents (e.g., bacteriophages) and one or more indicator genes. In some embodiments, compositions can include cocktails of different indicator phages that may encode and express the same or different indicator proteins. In some embodiments, the cocktail of bacteriophage comprises at least two different types of recombinant bacteriophages.

Methods of Preparing Indicator Bacteriophage

Embodiments of methods for making indicator bacteriophage begin with selection of a wild-type bacteriophage for genetic modification. Some bacteriophage are highly specific for a target bacterium. This presents an opportunity for highly specific detection.

Thus, the methods of the present disclosure utilize the high specificity of binding agents, associated with infectious agents that recognize and bind to a particular microorganism of interest as a means to amplify a signal and thereby detect low levels of a microorganism (e.g., a single microorganism) present in a sample. For example, infectious agents (e.g., bacteriophage) specifically recognize surface receptors of particular microorganisms and thus specifically infect those microorganisms. As such, these infectious agents may be appropriate binding agents for targeting a microorganism of interest. As discussed herein, the bacteriophage may replicate inside of the bacteria to generate hundreds of progeny phage. Detection of the product of an indicator gene inserted into the bacteriophage genome can be used as a measure of the bacteria in the sample.

Some embodiments of the disclosure utilize the specificity of binding and high-level genetic expression capacity of recombinant bacteriophage for rapid and sensitive targeting to infect and facilitate detection of a bacterium of interest. In some embodiments, the indicator bacteriophage is genetically modified to include a reporter gene. In some embodiments the late gene region of a bacteriophage is genetically modified to include an indicator (reporter) gene. In some embodiments, an indicator gene is positioned downstream of the major capsid gene. In other embodiments, an indicator gene is positioned upstream of the major capsid gene. In some embodiments, the inserted genetic construct further comprises its own exogenous, dedicated promoter to drive expression of the indicator gene. The exogenous promoter is in addition to any endogenous promoter in the phage genome. As bacteriophage produce polycistronic mRNA transcripts, only a single promoter is required upstream of the first gene/cistron in the transcript. Conventional recombinant constructs only use the endogenous bacteriophage promoter to drive inserted genes. In contrast, addition of an additional promoter upstream of the reporter gene and ribosomal binding site may increase gene expression by acting as a secondary initiation site for transcription. The complicated and compact genomes of viruses often have overlapping genes in different frames, sometimes in two different directions.

Some embodiments of methods for preparing a recombinant indicator bacteriophage include selecting a wild-type bacteriophage that specifically infects a target pathogenic bacterium such as Escherichia coli, Cronobacter spp., Salmonella spp., Listeria spp., or Staphylococcus spp.; preparing a homologous recombination plasmid/vector that comprises an indicator gene; transforming the homologous recombination plasmid/vector into target pathogenic bacteria; infecting the transformed target pathogenic bacteria with the selected wild-type bacteriophage, thereby allowing homologous recombination to occur between the plasmid/vector and the bacteriophage genome; and isolating a particular clone of recombinant bacteriophage.

Various methods for designing and preparing a homologous recombination plasmid are known. Various methods for transforming bacteria with a plasmid are known, including heat-shock, F pilus mediated bacterial conjugation, electroporation, and other methods. Various methods for isolating a particular clone following homologous recombination are also known. Some method embodiments described herein utilize particular strategies.

Thus, some embodiments of methods for preparing indicator bacteriophage include the steps of selecting a wild-type bacteriophage that specifically infects a target pathogenic bacterium; determining the natural sequence in the late region of the genome of the selected bacteriophage; annotating the genome and identifying the major capsid protein gene of the selected bacteriophage; designing a sequence for homologous recombination adjacent to the major capsid protein gene, wherein the sequence comprises a codon-optimized reporter gene; incorporating the sequence designed for homologous recombination into a plasmid/vector; transforming the plasmid/vector into target pathogenic bacteria; selecting for the transformed bacteria; infecting the transformed bacteria with the selected wild-type bacteriophage, thereby allowing homologous recombination to occur between the plasmid and the bacteriophage genome; determining the titer of the resulting recombinant bacteriophage lysate; and performing a limiting dilution assay to enrich and isolate the recombinant bacteriophage. Some embodiments comprise further repeating the limiting dilution and titer steps, following the first limiting dilution assay, as needed until the recombinant bacteriophage represent a detectable fraction of the mixture. For example, in some embodiments the limiting dilution and titer steps can be repeated until at least 1/30 of the bacteriophage in the mixture are recombinant before isolating a particular clone of recombinant bacteriophage. A ratio of 1:30 recombinant:wild-type is expected, in some embodiments, to yield an average of 3.2 transducing units (TU) per 96 plaques (e.g., in a 96-well plate). The initial ratio of recombinant to wild-type phage may be determined by performing limiting dilution assays based on the TCID50 (tissue culture infectious dose 50%) as previously described in U.S. application Ser. No. 15/409,258. By Poisson distribution, a 1:30 ratio generates a 96% chance of observing at least one TU somewhere in the 96 wells.

As noted herein, in certain embodiments, it may be preferred to utilize infectious agents that have been isolated from the environment for production of the infectious agents of the disclosure. In this way, infectious agents that are specific to naturally derived microorganisms may be generated.

There are numerous known methods and commercial products for preparing plasmids. For example, PCR, site-directed mutagenesis, restriction digestion, ligation, cloning, and other techniques may be used in combination to prepare plasmids. Synthetic plasmids can also be ordered commercially (e.g., GeneWiz). Cosmids can also be employed, or the CRISPR/CAS9 system could be used to selectively edit a bacteriophage genome. Some embodiments of methods of preparing a recombinant indicator bacteriophage include designing a plasmid that can readily recombine with the wild-type bacteriophage genome to generate recombinant genomes. In designing a plasmid, some embodiments include addition of a codon-optimized reporter gene, such as a luciferase gene. Some embodiments further include addition of elements into the upstream untranslated region. For example, in designing a plasmid to recombine with the indicator bacteriophage genome, an upstream untranslated region can be added between the sequence encoding the C-terminus of the gp23/Major Capsid Protein and the start codon of the indicator subunit, such as the HiBiT indicator gene. The untranslated region can include a promoter, such as a T7, T4, T4-like, Phage K, MP131, MP115, MP112, MP506, MP87, Rambo, SAPJV1 promoter. The untranslated region can also include a Ribosomal Entry/Binding Site (RBS), also known as a "Shine-Dalgarno Sequence" with bacterial systems. Either or both of these elements, or other untranslated elements, can be embedded within a short upstream untranslated region made of random sequences comprising about the same GC content as rest of the phage genome. The random region should not include an ATG sequence, as that will act as a start codon.

The MCP fragment is a part of a structural gene that encodes virion protein. As these virion proteins are expressed at a very high level, any genes inserted into this region can be expected to have similar expression levels, as long as late gene promoters and/or other similar control elements are used. In certain instances, the indicator (e.g., HiBiT) is fused to the major capsid protein. In some embodiments, the peptide tag (i.e., HiBiT) is fused to the N-terminus of the MCP. In other embodiments the peptide tag is fused to the C-terminus of the MCP.

In some embodiments, indicator bacteriophages are genetically engineered to comprise an indicator gene such as a subunit of a luciferase gene. For example, an indicator phage can be specific to a particular bacteria of interest, wherein the genome comprises the sequence of the HiBit gene. A recombinant indicator HiBit bacteriophage genome may further comprise a consensus promoter of T7, T4, T4-like, Phage K, MP131, MP115, MP112, MP506, MP87, Rambo, SAPJV1, ViI, or another late promoter. In further embodiments, the promoter is an exogenous promoter. Insertion of an exogenous promoter to drive expression of an indicator gene is advantageous in that expression is not limited by the expression of other phage proteins (e.g., the major capsid protein).

Thus, in the embodiment of the recombinant phage generated as a result of the recombination, the indicator gene or subunit gene (e.g., HiBiT) is inserted into the late gene region, just downstream of the gene encoding the major capsid protein, and thus creates recombinant bacteriophage genomes comprising the HiBiT gene. The construct may additionally comprise the consensus promoter of T7, T4, T4-like, Phage K, MP131, MP115, MP112, MP506, MP87, Rambo, SAPJV1, ViI, or another late promoter or another suitable promoter to drive transcription and expression of the luciferase gene. The construct may also comprise a composite untranslated region synthesized from several UTRs. This construct ensures soluble luciferase is produced such that expression is not limited to the number of capsid proteins inherent in the phage display system.

Recombinant phage generated by homologous recombination of a plasmid designed for recombination with the wild-type phage genome can be isolated from a mixture comprising a very small percentage (e.g., 0.005%) of total phage genomes. Following isolation, large scale production may be performed to obtain high titer recombinant indicator phage stocks appropriate for use in the detection assay. Furthermore, cesium chloride isopycnic density gradient centrifugation may be used to separate phage particles from contaminating luciferase protein to reduce background.

Methods of Using Infectious Agents for Detecting Bacteria

As noted herein, in certain embodiments, the disclosure may comprise methods of using infectious particles for detecting microorganisms. The methods of the disclosure may be embodied in a variety of ways.

In an embodiment, the invention may comprise a method for detecting a bacterium of interest in a sample comprising the steps of: incubating the sample with bacteriophage that infects the bacterium of interest, wherein the bacteriophage comprises an indicator gene or subunit of an indicator gene such that expression of the indicator gene or subunit during bacteriophage replication following infection of the bacterium of interest results in production of an indicator protein product; and detecting the indicator protein product, wherein positive detection of the indicator protein product indicates that the bacterium of interest is present in the sample. In some embodiments, the indicator protein product is a fusion protein. In other embodiments, the indicator protein product is a soluble, non-fusion protein.

In certain embodiments, the assay may be performed to utilize a general concept that can be modified to accommodate different sample types or sizes and assay formats. Embodiments employing indicator bacteriophage of the disclosure may allow rapid detection of specific bacterial strains such as *Escherichia coli, Cronobacter* spp., *Salmonella* spp *Listeria* spp., or *Staphylococcus* spp. with total assay times under 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12, 12.5, 13.0, 13.5, 14.0, 14.5, 15.0, 15.5, 16.0, 16.5, 17.0, 17.5, 18.0, 18.5, 19.0, 19.5, 20.0, 21.0, 21.5 22.0, 22.5, 23.0, 23.5, 24.0, 24.5 25.0, 25.5, or 26.0 hours, depending on the sample type, sample size, and assay format. For example, the amount of time required may be somewhat shorter or longer depending on the strain of bacteriophage and the strain of bacteria to be detected in the assay, type and size of the sample to be tested, conditions required for viability of the target, complexity of the physical/chemical environment, and the concentration of "endogenous" non-target bacterial contaminants.

In some embodiments, the phage (e.g., SEA1, TSP1, TSP12, T7, T4, T4-like, Phage K, MP131, MP115, MP112, MP506, MP87, Rambo, SAPJV1 phage) may be engineered to express an indicator gene or subunit during replication of the phage. Expression of the indicator gene is driven by a viral capsid promoter (e.g., the bacteriophage T7 or T4 late promoter), yielding high expression.

Parental phage will express the indicator protein or subunit (e.g., HiBit). Thus, there is generally a need to separate out the parental phage from the progeny phage or remove the indicator protein or subunit from parental bacteriophage, so that signal in the assay comes from replication of progeny phage during infection of the bacterial cells and not from parental phage.

In some embodiments, there is no background signal or substantially no background signal from the parental bacteriophage. In certain instances, the indicator or subunit (e.g., HiBiT) is non-luminescent or substantially non-luminescent. In further embodiments, the indicator or subunit is removed from parental bacteriophage prior to addition of a substrate, so the signal detected in the assay must come from replication of progeny phage during infection of the bacterial cells. Any method generally known in the art can be used to remove the indicator or subunit (e.g., HiBiT) from parental phage. For example, a protease-cleavable linker (cleavage tag) may be cloned into the parental phage. Selection of an appropriate cleavage tag depends on the selected bacteriophage. For example, the cleavage tag may be selected from the group comprising 3C (PreScission) (LEVLFQ/GP), EKT (enterokinase) (DDDDK/), FXa (Factor FXa) (IEGR/), TEV (tobacco etch virus) (ENLYFQ/G), and thrombin (LVPR/GS). The main cleavage site for each cleavage tag is indicated by the "/". Thus, in some embodiments, the indicator phage comprises a protease cut site. For example, the indicator phage may comprise a fusion of indicator subunit (peptide)-capsid protein containing a protease cut site. The protease cut site may be recombinant, i.e., added or created in the genetic modification process. In further embodiments, a protease is added to the parental bacteriophage. In some embodiments, the protease is added during phage preparation to remove the indicator subunit from the parental bacteriophage, thereby generating a soluble indicator subunit (peptide). In further embodiments, the protease is added after the phage have been concentrated. In certain instances, the protease is added prior to purification purified to remove any residual indicator protein that may be generated upon production of the infectious agent stock.

The selected protease is specific to the cleavage tag. 3C, EKT, FXa, TEV, and thrombin cleavage tags may be cleaved by human rhinovirus (HRV), enterokinase, Factor FXa, tobacco etch virus protease, and thrombin, respectively. The specificity of each cleavage enzyme varies. For example, HRV is a highly specific protease that cleaves between the Glu and Gly residues in the cleavage tag. Enterokinase is an intestinal enzyme normally involved in the protease cleavage of Trypsin. It cleaves after the Lysine (K) in is recognition sequence. Factor Xa cleaves after the Arg residue but can also cleave less frequently at secondary basic sites. Its most common secondary cleavage site is between the Gly and Arg residues in its own recognition site, although the frequency of these events is protein specific. Cleavage by TEV occurs between the Glu and Gly residues. TEV is often reported to have better specificity for its recognition site compared to EKT, Thrombin or Factor Xa. Thrombin cleaves preferentially between the Arg and Gly residues. Off target cleavage can occur at non-specific sites, normally from contaminating proteases. To ensure maximal protein integrity the enzyme reagent must be very pure.

In some embodiments, the sample may be enriched prior to testing by incubation in conditions that encourage growth. In such embodiments, the enrichment period can be 1, 2, 3, 4, 5, 6, 7, 8, 9, 10, 11, 12, 13, 14, 15, or 16 hours or longer, depending on the sample type and size.

In some embodiments, the indicator bacteriophage comprises an indicator gene, and infection of a single pathogenic cell (e.g., bacterium) can be detected by an amplified signal generated via the expression of the indicator gene. Thus, the method may comprise detecting an indicator protein produced during phage replication, wherein detection of the indicator protein indicates that the bacterium of interest is present in the sample.

In an embodiment, the disclosure may comprise a method for detecting a bacterium of interest in a sample comprising the steps of: incubating the sample with an indicator bacteriophage that infects the bacterium of interest, wherein the indicator bacteriophage comprises an indicator gene inserted into a late gene region of the bacteriophage such that expression of the indicator gene during bacteriophage replication following infection of host bacteria results in production of an indicator protein product; incubating the indicator protein product with a detection reagent, wherein the detection reagent comprises a polypeptide complementary to the indicator protein product, and wherein the indicator protein product and its complementary polypeptide for an indicator complex; and detecting the indicator complex, wherein positive detection of the indicator complex indicates that the bacterium of interest is present in the sample. In some embodiments, the amount of indicator detected corresponds to the amount of the bacterium of interest present in the sample.

As described in more detail herein, the methods and systems of the disclosure may utilize a range of concentrations of parental indicator bacteriophage to infect bacteria present in the sample. In some embodiments the indicator bacteriophage are added to the sample at a concentration sufficient to rapidly find, bind, and infect target bacteria that are present in very low numbers in the sample, such as a single cell. In some embodiments, the phage concentration can be sufficient to find, bind, and infect the target bacteria in less than one hour. In other embodiments, these events can occur in less than two hours, or less than three hours, following addition of indicator phage to the sample. For example, in certain embodiments, the bacteriophage concentration for the incubating step is greater than $1\times10^5$ PFU/mL, greater than $1\times10^6$ PFU/mL, or greater than $1\times10^7$ PFU/mL.

In certain embodiments, the infectious agent may be purified so as to be free of any residual indicator protein that may be generated upon production of the infectious agent stock. Thus, in certain embodiments, the indicator bacteriophage may be purified using cesium chloride isopycnic density gradient centrifugation prior to incubation with the sample. When the infectious agent is a bacteriophage, this purification may have the added benefit of removing bacteriophage that do not have DNA (i.e., empty phage or "ghosts").

In some embodiments of the methods of the disclosure, the microorganism may be detected without any isolation or purification of the microorganisms from a sample. For example, in certain embodiments, a sample containing one or a few microorganisms of interest may be applied directly to an assay container such as a spin column, a microtiter well, or a filter and the assay is conducted in that assay container. Various embodiments of such assays are disclosed herein.

Aliquots of a test sample may be distributed directly into wells of a multi-well plate, indicator phage may be added, and after a period of time sufficient for infection, a lysis buffer may be added as well as a substrate for the indicator protein (e.g., luciferase substrate for a luciferase indicator) and assayed for detection of the indicator signal. Some embodiments of the method can be performed on filter plates. Some embodiments of the method can be performed with or without concentration of the sample before infection with indicator phage.

For example, in many embodiments, multi-well plates are used to conduct the assays. The choice of plates (or any other container in which detecting may be performed) may affect the detecting step. For example, some plates may include a colored or white background, which may affect the detection of light emissions. Generally speaking, white plates have higher sensitivity but also yield a higher background signal. Other colors of plates may generate lower background signal but also have a slightly lower sensitivity. Additionally, one reason for background signal is the leakage of light from one well to another, adjacent well. There are some plates that have white wells but the rest of the plate is black. This allows for a high signal inside the well but prevents well-to-well light leakage and thus may decrease background. Thus the choice of plate or other assay vessel may influence the sensitivity and background signal for the assay.

Methods of the disclosure may comprise various other steps to increase sensitivity. For example, as discussed in more detail herein, the method may comprise a step for washing the captured and infected bacterium, after adding the bacteriophage but before incubating, to remove excess parental bacteriophage and/or luciferase or other reporter protein contaminating the bacteriophage preparation.

In some embodiments, detection of the microorganism of interest may be completed without the need for culturing the sample as a way to increase the population of the microorganisms. For example, in certain embodiments the total time required for detection is less than 26.0, 25.0, 24.0, 23.0, 22.0, 21.0, 20.0, 19.0, 18.0, 17.0, 16.0 hours, 15.0 hours, 14.0 hours, 13.0 hours, 12.0 hours, 11.0 hours, 10.0 hours, 9.0 hours, 8.0 hours, 7.0 hours, 6.0 hours, 5.0 hours, 4.0 hours, 3.0 hours, 2.5 hours, 2.0 hours, 1.5 hours, 1.0 hour, 45 minutes, or less than 30 minutes. Minimizing time to result is critical in food and environmental testing for pathogens.

In contrast to assays known in the art, the method of the disclosure can detect individual microorganisms. Thus, in certain embodiments, the method may detect ≤10 cells of the microorganism (i.e., 1, 2, 3, 4, 5, 6, 7, 8, 9 microorganisms) present in a sample. For example, in certain embodiments, the indicator bacteriophage is highly specific for a particular bacteria of interest. In an embodiment, the recombinant bacteriophage can distinguish the bacteria of interest in the presence of other types of bacteria. In certain embodiments, the recombinant bacteriophage can be used to detect a single bacterium of the specific type in the sample. In certain embodiments, the recombinant bacteriophage detects as few as 2, 3, 4, 5, 6, 7, 8, 9, 10, 15, 20, 30, 40, 50, 60, 70, 80, 90, or 100 of the specific bacteria in the sample.

Thus, aspects of the present disclosure provide methods for detection of microorganisms in a test sample via an indicator complex. In some embodiments, where the microorganism of interest is a bacterium, one or more subunits of the indicator complex may be associated with an infectious agent such as an indicator bacteriophage. The indicator complex may react with a substrate to emit a detectable signal or may emit an intrinsic signal (e.g., fluorescent protein). In some embodiments, the detection sensitivity can reveal the presence of as few as 50, 20, 10, 9, 8, 7, 6, 5, 4, 3, or 2 cells of the microorganism of interest in a test sample. In some embodiments, even a single cell of the microorganism of interest may yield a detectable signal. In some embodiments, the bacteriophage is a T4-like or ViI-like bacteriophage.

In some embodiments, the indicator protein encoded by the infectious agent may be detectable during or after replication of the infectious agent. Many different types of detectable biomolecules suitable for use as indicator moieties are known in the art, and many are commercially available. In some embodiments the indicator phage comprises an indicator gene encoding an enzyme, which serves as the indicator protein. In other embodiments, the indicator phage comprises an indicator gene encoding a subunit of an enzyme, which serves as the indicator moiety. In some embodiments, the genome of the indicator phage is modified to encode a soluble, non-fusion protein. In other embodiments, the genome of the indicator phage is modified to encode a fusion protein. In some embodiments, the indicator phage encodes a subunit of a detectable enzyme (i.e., indicator protein product). In some embodiments, the subunit of the detectable enzyme is incubated in the presence of a complementary subunit of the detectable enzyme such that they reconstitute to form a functional enzyme (i.e., indicator complex). The indicator complex may emit light and/or may be detectable by a color change in an added substrate. Various appropriate enzymes are commercially available, such as alkaline phosphatase (AP), horseradish peroxidase (HRP), or luciferase (Luc). In some embodiments, these enzymes may serve as the indicator protein. In some embodiments, Firefly luciferase is the detectable enzyme. In some embodiments, Oplophorus luciferase is the detectable enzyme. In some embodiments, NANOLUC® is the detectable enzyme. In some embodiments, a HiBiT-LgBiT complex is the detectable enzyme. In some embodiments, is the detectable enzyme. Other engineered luciferases or other enzymes that generate detectable signals may also be used with the embodiments described in detail herein.

In some embodiments, the indicator gene encodes a subunit of a protein capable of emitting an intrinsic signal, such as a fluorescent protein (e.g., green fluorescent protein or others). The subunit (labeling subunit) of the indicator protein may reconstitute with a second subunit of the protein (detection subunit) to form an indicator complex. The indicator complex may emit light and/or may be detectable by a color change. In some embodiments, the indicator complex is a functional enzyme (e.g., luciferase) that interacts with a substrate to generate signal. In some embodiments, the labeling subunit is a subunit of a luciferase gene. In some embodiments, the luciferase gene is one of Oplophorus luciferase, Firefly luciferase, *Renilla* luciferase, *Gaussia* luciferase, Lucia luciferase, or an engineered luciferase such as NANOLUC®, NANOBIT®, Rluc8.6-535, or Orange Nano-lantern.

Detecting the indicator may include detecting emissions of light. In some embodiments, a luminometer may be used to detect the reaction of indicator (e.g., luciferase) with a substrate. The detection of RLU can be achieved with a luminometer, or other machines or devices may also be used. For example, a spectrophotometer, CCD camera, or CMOS camera may detect color changes and other light emissions. Absolute RLU are important for detection, but the signal to background ratio also needs to be high (e.g., >2.0, >2.5, or >3.0) in order for single cells or low numbers of cells to be detected reliably.

In some embodiments, the indicator phage is genetically engineered to contain a subunit of a gene for an enzyme, such as a luciferase. Thus, the enzyme (e.g., luciferase) is only produced upon infection of bacteria that the phage specifically recognizes and infects and the subsequent reconstitution of the labeling subunit expressed on progeny bacteriophage with the detection subunit. In certain instances, the indicator moiety is expressed late in the viral life cycle. In some embodiments, the indicator is a fusion protein. In other embodiments, as described herein, the indicator is a soluble protein (e.g., soluble luciferase) and is not fused with a phage structural protein that limits its copy number.

Thus in some embodiments utilizing indicator phage, the disclosure comprises a method for detecting a microorganism of interest comprising the steps of capturing at least one sample bacterium; incubating the at least one bacterium with a plurality of indicator phage; allowing time for infection and replication to generate progeny phage and express indicator moiety; reconstituting the indicator moiety with the detection subunit, thereby forming an indicator complex; and detecting the progeny phage, or preferably the indicator complex, wherein detection of the indicator complex demonstrates that the bacterium is present in the sample.

For example, in some embodiments the test sample bacterium may be captured by binding to the surface of a plate, or by filtering the sample through a bacteriological filter (e.g., 0.45 μm pore size spin filter or plate filter). In an embodiment, the infectious agent (e.g., indicator phage) is added in a minimal volume to the captured sample directly on the filter. In an embodiment, the microorganism captured on the filter or plate surface is subsequently washed one or more times to remove excess unbound infectious agent. In an embodiment, a medium (e.g., Luria-Bertani Broth, also called LB herein, Buffered Peptone Water, also called BPW herein, or Tryptic Soy Broth or Tryptone Soy Broth, also called TSB herein) may be added for further incubation time, to allow replication of bacterial cells and phage and high-level expression of the gene encoding the indicator moiety. However, a surprising aspect of some embodiments of testing assays is that the incubation step with indicator phage only needs to be long enough for a single phage life cycle. The amplification power of using bacteriophage was previously thought to require more time, such that the phage would replicate for several cycles. A single replication cycle of indicator phage can be sufficient to facilitate sensitive and rapid detection according to some embodiments of the present disclosure.

In some embodiments, aliquots of a test sample comprising bacteria may be applied to a spin column and after infection with a recombinant bacteriophage and an optional washing to remove any excess bacteriophage, the amount of soluble indicator detected will be proportional to the amount of bacteriophage that are produced by infected bacteria.

In some embodiments, the progeny phage are lysed prior to incubation with a detection reagent comprising the detection subunit. In some embodiments, the detection reagent further comprises a substrate. For example, in detection systems utilizing Nano-Glo HiBiT Lytic Detection System technology, progeny bacteriophage expressing HiBiT must be lysed in order for the complementary polypeptide, LgBiT, to access HiBiT. When HiBiT encounters LgBiT they reconstitute to form a functional luciferase enzyme.

Soluble indicator released into the surrounding liquid upon lysis of the bacteria may then be measured and quantified. In an embodiment, the solution is spun through the filter, and the filtrate collected for assay in a new receptacle (e.g., in a luminometer) following addition of a substrate for the indicator enzyme (e.g., luciferase substrate). Alternatively, the indicator signal may be measured directly on the filter.

In various embodiments, the purified parental indicator phage does not comprise the detectable indicator itself, because the parental phage can be purified before it is used for incubation with a test sample. Expression of late (Class III) genes occurs late in the viral life cycle. In some embodiments of the present disclosure, parental phage may be purified to exclude any existing indicator protein (e.g., luciferase). In some embodiments, expression of the indicator gene during bacteriophage replication following infection of host bacteria results in a soluble indicator protein product. Thus, in many embodiments, it is not necessary to separate parental from progeny phage prior to the detecting step. In an embodiment, the microorganism is a bacterium and the indicator phage is a bacteriophage. In an embodiment, the indicator protein is soluble luciferase, which is released upon lysis of the host microorganism.

Thus, in an alternate embodiment, the indicator substrate (e.g., luciferase substrate) may be incubated with the portion of the sample that remains on a filter or bound to a plate surface. Accordingly, in some embodiments the solid support is a 96-well filter plate (or regular 96-well plate), and the substrate reaction may be detected by placing the plate directly in the luminometer.

For example, in an embodiment, the disclosure may comprise a method for detecting *Salmonella* spp. comprising the steps of: infecting cells captured on a 96-well filter plate with a plurality of parental indicator phage capable of expressing luciferase upon infection; washing excess phage away; adding LB broth and allowing time for phage to replicate and lyse the specific *Salmonella* spp. target (e.g., 30-120 minutes); and detecting the indicator luciferase by adding luciferase substrate and measuring luciferase activity directly in the 96-well plate, wherein detection of luciferase activity indicates that the *Salmonella* spp. is present in the sample.

In another embodiment, the disclosure may comprise a method for detecting *Salmonella* spp. comprising the steps of: infecting cells in liquid solution or suspension in a 96-well plate with a plurality of parental indicator phage capable of expressing the indicator gene upon infection; allowing time for phage to replicate and lyse the specific *Salmonella* spp. target (e.g., 30-120 minutes); and detecting the indicator luciferase by adding luciferase substrate and measuring luciferase activity directly in the 96-well plate, wherein detection of luciferase activity indicates that the *Salmonella* spp. is present in the sample. In such an embodiment no capturing step is necessary. In some embodiments, the liquid solution or suspension may be a consumable test sample, such as a vegetable wash. In some embodiments, the liquid solution or suspension may be vegetable wash fortified with concentrated LB Broth, Tryptic/Tryptone Soy Broth, Peptone Water or Nutrient Broth. In some embodiments, the liquid solution or suspension may be bacteria diluted in LB Broth.

In some embodiments, the reaction of indicator protein (e.g., luciferase) with substrate may continue for 30 minutes or more, and detection at various time points may be desirable for optimizing sensitivity. For example, in embodiments using 96-well filter plates as the solid support and luciferase as the indicator, luminometer readings may be taken initially and at 10- or 15-minute intervals until the reaction is completed.

Surprisingly, high concentrations of phage utilized for infecting test samples have successfully achieved detection of very low numbers of target microorganism in a very short timeframe. The incubation of phage with a test sample in some embodiments need only be long enough for a single phage life cycle. In some embodiments, the bacteriophage concentration for this incubating step is greater than $7 \times 10^6$, $8 \times 10^6$, $9 \times 10^6$, $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $3.0 \times 10^7$, $4.0 \times 10^7$, $5.0 \times 10^7$, $6.0 \times 10^7$, $7.0 \times 10^7$, $8.0 \times 10^7$, $9.0 \times 10^7$, or $1.0 \times 10^8$ PFU/mL.

Success with such high concentrations of phage is surprising because the large numbers of phage were previously associated with "lysis from without," which killed target cells and thereby prevented generation of useful signal from earlier phage assays. It is possible that the clean-up of prepared phage stocks described herein helps to alleviate this problem (e.g., clean-up by cesium chloride isopycnic density gradient ultracentrifugation), because in addition to removing any contaminating indicator gene associated with the phage, this clean-up may also remove ghost particles (particles that have lost DNA). The ghost particles can lyse bacterial cells via "lysis from without," killing the cells prematurely and thereby preventing generation of indicator signal. Electron microscopy demonstrates that a crude phage lysate (i.e., before cesium chloride clean-up) may have greater than 50% ghosts. These ghost particles may contribute to premature death of the microorganism through the action of many phage particles puncturing the cell membrane. Thus ghost particles may have contributed to previous problems where high PFU concentrations were reported to be detrimental. Moreover, a very clean phage prep allows the assay to be performed with no wash steps, which makes the assay possible to perform without an initial concentration step. Some embodiments do include an initial concentration step, and in some embodiments this concentration step allows a shorter enrichment incubation time.

Some embodiments of testing methods may further include confirmatory assays. A variety of assays are known in the art for confirming an initial result, usually at a later point in time. For example, the samples can be cultured (e.g., CHROMAGAR®, DYNABEADS® assay, PCR can be utilized to confirm the presence of the microbial DNA, or other confirmatory assays can be used to confirm the initial result.

In certain embodiments, the methods of the present disclosure combine the use of a binding agent (e.g., antibody) to purify and/or concentrate a microorganism of interest from the sample in addition to detection with an infectious agent. For example, in certain embodiments, the present disclosure comprises a method for detecting a microorganism of interest in a sample comprising the steps of: capturing the microorganism from the sample on a prior support using a capture antibody specific to the microorganism of interest; incubating the sample with a recombinant indicator bacteriophage comprising an indicator gene, wherein the indicator gene encodes a first subunit of an indicator protein, thereby producing an amount of progeny phage expressing the first subunit; lysing the amount of progeny phage; incubating the lysed progeny phage in the presence of a detection reagent, wherein the detection reagent comprises a second subunit of an indicator protein, thereby allowing the first subunit and second subunit to reconstitute to form an indicator protein complex; and detecting the indicator protein complex, wherein positive detection of the indicator protein complex indicates that the particular bacteria of interest is present in the sample. In some embodiments synthetic phage are designed to optimize desirable traits for use in pathogen detection assays. In some embodiments bioinformatics and previous analyses of genetic modifications are employed to optimize desirable traits. For example, in some embodiments, the genes encoding phage tail proteins can be optimized to recognize and bind to particular species of bacteria. In other embodiments the genes encoding phage tail proteins can be optimized to recognize and bind to an entire genus of bacteria, or a particular group of species within a genus. In this way, the phage can be optimized to detect broader or narrower groups of pathogens. In some embodiments, the synthetic phage may be designed to improve expression of the reporter gene. Additionally and/or alternatively, in some instances, the synthetic phage may be designed to increase the burst size of the phage to improve detection.

In some embodiments, the stability of the phage may be optimized to improve shelf-life. For example, enzybiotic solubility may be increased in order to increase subsequent phage stability. Additionally and/or alternatively phage thermostability may be optimized. Thermostable phage better preserve functional activity during storage thereby increasing shelf-life. Thus, in some embodiments, the thermostability and/or pH tolerance may be optimized.

Systems and Kits of the Disclosure

In some embodiments, the disclosure comprises systems (e.g., automated systems or kits) comprising components for performing the methods disclosed herein. In some embodiments, indicator phage are comprised in systems or kits according to the disclosure. Methods described herein may also utilize such indicator phage systems or kits. Some embodiments described herein are particularly suitable for automation and/or kits, given the minimal amount of reagents and materials required to perform the methods. In certain embodiments, each of the components of a kit may comprise a self-contained unit that is deliverable from a first site to a second site.

In some embodiments, the disclosure comprises systems or kits for rapid detection of a microorganism of interest in a sample. The systems or kits may in certain embodiments comprise a component for incubating the sample with an infectious agent specific for the microorganism of interest, wherein the infectious agent comprises an indicator gene and a component for detecting the indicator protein. In some embodiments of both the systems and the kits of the disclosure, the infectious agent is a recombinant bacteriophage that infects the bacterium of interest, and the recombinant bacteriophage comprises an indicator gene encoding a peptide or polypeptide subunit of an indicator protein. In some embodiments, the indicator gene inserted into a late gene region of the bacteriophage is the indicator moiety such that expression of the indicator gene during bacteriophage replication following infection of host bacteria results in a subunit of an indicator protein product. Thus, some systems further comprise a detection reagent, wherein the detection reagent comprises a polypeptide subunit of an indicator protein, wherein the polypeptide subunit reconstitutes with the peptide subunit to form an indicator protein complex, and a substrate for reacting with an indicator protein complex to detect the indicator protein complex. Additionally, some systems further comprise a component for capturing the microorganism of interest on a solid support.

In other embodiments, the disclosure comprises a method, system, or kit for rapid detection of a microorganism of interest in a sample, comprising an infectious agent component that is specific for the microorganism of interest, wherein the infectious agent comprises an indicator moiety, and a component for detecting the indicator protein. In certain embodiments, the recombinant bacteriophage is highly specific for a particular bacterium.

In certain embodiments, the systems and/or kits may further comprise a component for washing the captured microorganism sample. Additionally or alternatively, the systems and/or kits may further comprise a component for determining amount of the indicator moiety, wherein the amount of indicator moiety detected corresponds to the amount of microorganism in the sample. For example, in certain embodiments, the system or kit may comprise a luminometer or other device for measuring a luciferase enzyme activity.

In some systems and/or kits, the same component may be used for multiple steps. In some systems and/or kits, the steps are automated or controlled by the user via computer input and/or wherein a liquid-handling robot performs at least one step.

Thus in certain embodiments, the disclosure may comprise a system or kit for rapid detection of a microorganism of interest in a sample, comprising: a component for incubating the sample with an infectious agent specific for the microorganism of interest, wherein the infectious agent comprises an indicator moiety; a component for capturing the microorganism from the sample on a solid support; a component for washing the captured microorganism sample to remove unbound infectious agent; and a component for detecting the indicator moiety. In some embodiments, the same component may be used for steps of capturing and/or incubating and/or washing (e.g., a filter component). Some embodiments additionally comprise a component for determining amount of the microorganism of interest in the sample, wherein the amount of indicator moiety detected corresponds to the amount of microorganism in the sample. Such systems can include various embodiments and subembodiments analogous to those described above for methods of rapid detection of microorganisms. In an embodiment, the microorganism is a bacterium and the infectious agent is a bacteriophage. In a computerized system, the system may be fully automated, semi-automated, or directed by the user through a computer (or some combination thereof).

In some embodiments, the system may comprise a component for isolating the microorganism of interest from the other components in the sample.

In an embodiment, the disclosure comprises a system or kit comprising components for detecting a microorganism of interest comprising: a component for isolating at least one microorganism from other components in the sample; a component for infecting at least one microorganism with a plurality of a parental infectious agent; a component for lysing the at least one infected microorganism to release progeny infectious agents present in the microorganism; and a component for detecting the progeny infectious agents, or with greater sensitivity, a soluble protein encoded and expressed by the infectious agent, wherein detection of the infectious agent or a protein product of the infectious agent, or a subunit thereof, indicates that the microorganism is present in the sample. In some embodiments, the system or kit may further include a component for reconstituting the subunit of the protein product of the infectious agent to form a detectable indicator protein complex The infectious agent may comprise bacteriophage carrying the HiBiT indicator gene.

In other embodiments, the disclosure may comprise a kit for rapid detection of a microorganism of interest in a sample, the system comprising: a component for incubating the sample with an infectious agent specific for the microorganism of interest, wherein the infectious agent comprises a subunit of an indicator protein; a component for capturing the microorganism from the sample on a solid support; a component for washing the captured microorganism sample to remove unbound infectious agent; and a component for detecting the indicator protein (i.e., a detection reagent). In some embodiments, the detection reagent comprises a polypeptide subunit of an indicator protein, wherein the polypeptide subunit reconstitutes with the peptide subunit to form an indicator protein complex, and a substrate for reacting with an indicator protein complex to detect the indicator protein complex. The same component may be used for steps of capturing and/or incubating and/or washing. Some embodiments additionally comprise a component for determining amount of the microorganism of interest in the sample, wherein the amount of the indicator protein complex detected corresponds to the amount of microorganism in the sample. Such kits can include various embodiments and subembodiments analogous to those described above for methods of rapid detection of microorganisms. In an embodiment, the microorganism is a bacterium and the infectious agent is a bacteriophage.

In some embodiments, a kit may comprise a component for capturing the microorganism of interest.

In some embodiments, a kit may comprise a component for isolating the microorganism of interest from the other components in the sample.

These systems and kits of the disclosure include various components. As used herein, the term "component" is broadly defined and includes any suitable apparatus or collections of apparatuses suitable for carrying out the recited method. The components need not be integrally connected or situated with respect to each other in any particular way. The disclosure includes any suitable arrangements of the components with respect to each other. For example, the components need not be in the same room. But in some embodiments, the components are connected to each other in an integral unit. In some embodiments, the same components may perform multiple functions.

Computer Systems and Computer Readable Media

The system, as described in the present technique or any of its components, may be embodied in the form of a computer system. Typical examples of a computer system include a general-purpose computer, a programmed microprocessor, a microcontroller, a peripheral integrated circuit element, and other devices or arrangements of devices that are capable of implementing the steps that constitute the method of the present technique.

A computer system may comprise a computer, an input device, a display unit, and/or the Internet. The computer may further comprise a microprocessor. The microprocessor may be connected to a communication bus. The computer may also include a memory. The memory may include random access memory (RAM) and read only memory (ROM). The computer system may further comprise a storage device. The storage device can be a hard disk drive or a removable storage drive such as a floppy disk drive, optical disk drive, etc. The storage device can also be other similar means for loading computer programs or other instructions into the computer system. The computer system may also include a communication unit. The communication unit allows the computer to connect to other databases and the Internet through an I/O interface. The communication unit allows the transfer to, as well as reception of data from, other databases. The communication unit may include a modem, an Ethernet card, or any similar device which enables the computer system to connect to databases and networks such as LAN, MAN, WAN and the Internet. The computer system thus may facilitate inputs from a user through input device, accessible to the system through I/O interface.

A computing device typically will include an operating system that provides executable program instructions for the general administration and operation of that computing device, and typically will include a computer-readable storage medium (e.g., a hard disk, random access memory, read only memory, etc.) storing instructions that, when executed by a processor of the server, allow the computing device to perform its intended functions. Suitable implementations for the operating system and general functionality of the computing device are known or commercially available, and are readily implemented by persons having ordinary skill in the art, particularly in light of the disclosure herein.

The computer system executes a set of instructions that are stored in one or more storage elements, in order to process input data. The storage elements may also hold data or other information as desired. The storage element may be in the form of an information source or a physical memory element present in the processing machine.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers, or other network devices may be stored locally and/or remotely, as appropriate. Where a system includes computing devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optical storage devices, and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Non-transient storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

A computer-readable medium may comprise, but is not limited to, an electronic, optical, magnetic, or other storage device capable of providing a processor with computer-readable instructions. Other examples include, but are not limited to, a floppy disk, CD-ROM, DVD, magnetic disk, memory chip, ROM, RAM, SRAM, DRAM, content-addressable memory ("CAM"), DDR, flash memory such as NAND flash or NOR flash, an ASIC, a configured processor, optical storage, magnetic tape or other magnetic storage, or any other medium from which a computer processor can read instructions. In one embodiment, the computing device may comprise a single type of computer-readable medium such as random access memory (RAM). In other embodiments, the computing device may comprise two or more types of computer-readable medium such as random access memory (RAM), a disk drive, and cache. The computing device may be in communication with one or more external computer-readable mediums such as an external hard disk drive or an external DVD or Blu-Ray drive.

As discussed above, the embodiment comprises a processor which is configured to execute computer-executable program instructions and/or to access information stored in memory. The instructions may comprise processor-specific instructions generated by a compiler and/or an interpreter from code written in any suitable computer-programming language including, for example, C, C++, C#, Visual Basic, Java, Python, Perl, JavaScript, and ActionScript (Adobe Systems, Mountain View, Calif.). In an embodiment, the computing device comprises a single processor. In other embodiments, the device comprises two or more processors. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

The computing device comprises a network interface. In some embodiments, the network interface is configured for communicating via wired or wireless communication links. For example, the network interface may allow for communication over networks via Ethernet, IEEE 802.11 (Wi-Fi), 802.16 (Wi-Max), Bluetooth, infrared, etc. As another example, network interface may allow for communication over networks such as CDMA, GSM, UMTS, or other cellular communication networks. In some embodiments, the network interface may allow for point-to-point connections with another device, such as via the Universal Serial Bus (USB), 1394 FireWire, serial or parallel connections, or similar interfaces. Some embodiments of suitable computing devices may comprise two or more network interfaces for communication over one or more networks. In some embodiments, the computing device may include a data store in addition to or in place of a network interface.

Some embodiments of suitable computing devices may comprise or be in communication with a number of external or internal devices such as a mouse, a CD-ROM, DVD, a keyboard, a display, audio speakers, one or more microphones, or any other input or output devices. For example, the computing device may be in communication with various user interface devices and a display. The display may use any suitable technology including, but not limited to, LCD, LED, CRT, and the like.

The set of instructions for execution by the computer system may include various commands that instruct the processing machine to perform specific tasks such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing, or a request made by another processing machine.

While the present disclosure has been disclosed with references to certain embodiments, numerous modifications, alterations and changes to the described embodiments are possible without departing from the scope and spirit of the present disclosure, as defined in the appended claims. Accordingly, it is intended that the present disclosure not be limited to the described embodiments, but that it have the full scope defined by the language of the following claims, and equivalents thereof.

EXAMPLES

The following example describe methods Results depicted in the following examples demonstrate detection of a low number of cells, even a single bacterium, in a shortened time to results.

Example 1. Soluble TSP12.Hibit Expression in *Salmonella*

A soluble HiBiT TSP12 construct was cloned into pUC57.Amp plasmid giving TSP12.HR.HiBiT The plasmid was transformed into *Salmonella bongori* ATCC 43975 and transformants were selected on LB carbenicillin selective agar. Well isolated colonies were selected and inoculated into selective broth and incubated for 2 hours. Following incubation, 5 µL of culture was assayed to determine HiBiT expression using the HiBiT Lytic Assay Kit according to the manufacturer's instructions. The detected signal ranged from 11,000-100,000 RLUs/5 uL of culture (Table 1). The plasmid contained all necessary elements (promoter/RBS and coding sequence) for soluble HiBiT expression in *S. bongori* 43975.

TABLE 1

HiBiT signal of *S. bongori* transformants.

| | | | |
|---|---|---|---|
| A | 107079 | 11092 | X |
| B | 848 | 46074 | X |
| C | 98707 | 31093 | X |
| D | 99328 | 12559 | X |
| E | 70491 | 15515 | X |
| F | X | X | X |
| G | X | X | X |
| H | X | X | X |
| A | 1 | 6 | |
| B | 2 | 7 | |
| C | 3 | 8 | |
| D | 4 | 9 | |
| E | 5 | 10 | |
| F | | TSP12. HiBiT | |
| G | | | |
| H | | | |

The *S. bongori* transformant with the highest HiBit signal was then infected with wild type TSP12 at a multiplicity of infection (MOI) of 0.1. The phage lysate was clarified, filtered, and buffered exchanged. Serial dilutions of phage and phage with host cells was performed. Serial dilutions were then analyzed using TU50 assay and PFU titers were determined (Table 2).

TABLE 2

Soluble TSP12.HiBit Homologous Recombination Screen
*Salmonella bongori* 43975

| Phage Dilution | No. cells | 50 uL cells | | | | | Score | |
|---|---|---|---|---|---|---|---|---|
| 1E−08 | 566 | 935 | 1059 | 746 | 845 | 901 | 0.0 | |
| 1E−07 | 556 | 775 | 740 | 664 | 696 | 716 | 0.0 | |
| 1E−06 | 602 | 810 | 740 | 736 | 711 | 779 | 0.0 | |
| 1E−05 | 528 | 1779870 | 2763 | 1599 | 1417 | 1960 | 0.8 | |
| 1E−04 | 563 | 2163 | 3303 | 2450 | 2716 | 2533 | 1.0 | |
| 1E−03 | 645 | 9259 | 2291 | 2590 | 2634 | 1857 | 1.0 | |
| 1E−02 | 587 | 2118 | 2387 | 2750 | 2228 | 2384 | 1.0 | |
| 1E−01 | 522 | 1689 | 1605 | 1816 | 1718 | 1725 | 1.0 | |
| | | | | | | | 4.8 | Sum |
| | | | | | | | 2.00E+04 | $TU_{50}$(100 uL) |
| | | | | | | | 2.00E+05 | $TU_{50}$/mL |
| | | | | | | | 3.83E+03 | Ratio |

Example 2. TSP12.MCP-PS-HiBit Expression in Salmonella

A TSP12 major capsid protein (MCP) HiBiT fusion construct was cloned into pUC57.Amp plasmid. Cloning and sequence verification were performed using GeneWiz. The plasmid was reconstituted and lyophilized. Reconstituted, lyophilized plasmid was then transformed into *Salmonella bongori* ATCC 43975. Transformants were cultured and selected on LB carbenicillin selective agar. Isolated colonies were selected and inoculated into selective broth and incubated for 2 hours at 37° C. Following incubation, 5 uL of culture was assayed to determine HiBiT expression using the HiBiT Lytic Assay Kit according to the manufacturer's instructions. The detected HiBiT signal from transformants was approximately 800 RLUs/5 uL of culture (Table 3). The plasmid did not contain all necessary elements for efficient MCP-HiBiT expression in *S. bongori* ATCC 43975. In order for full expression of the HiBit fusion protein to occur, the plasmid must be recombined with TSP12 phage.

TABLE 3

HiBiT signal of *S. bongori* transformants.

| | | | |
|---|---|---|---|
| A | X | 891 | 869 |
| B | X | 90298 | 869 |
| C | X | 811 | 818 |
| D | X | 801 | 824 |
| E | X | 823 | 864 |
| F | X | X | X |
| G | X | X | X |
| H | X | X | X |
| A | | 1 | 6 |
| B | | 2 | 7 |
| C | | 3 | 8 |
| D | | 4 | 9 |
| E | | 5 | 10 |
| F | | TSP12. MCP- | |
| G | | PS-HiBiT | |
| H | | | |

The *S. bongori* transformant with the highest HiBit signal was then infected with wild type TSP12 at a multiplicity of infection (MOI) of 0.1. The phage lysate was clarified, filtered, and buffered exchanged. Serial dilutions of phage and phage with hoist cells was performed. Serial dilutions were then analyzed using TU50 assay and PFU titers were determined (Table 4). The recombinant phage was detected at 20-80 time the background signal (no cell control). The signal was dose dependent and increased with an increase in the number of phage.

| TSP12.MCP-PS-HiBit Homologous Recombination Screen *S. bongori* 43975 | | | | | | | |
|---|---|---|---|---|---|---|---|
| Phage Dilution | # cells | | 50 uL cells | | | Score | |
| 1E−08 | 591 | 787 | 912 | 804 | 633898 | 1072 | 0.2 |
| 1E−07 | 574 | 789 | 961 | 956 | 701 | 716 | 0.0 |
| 1E−06 | 604 | 856 | 1012 | 740 | 656 | 699 | 0.0 |
| 1E−05 | 536 | 3175 | 957 | 981 | 1309 | 1121 | 0.2 |
| 1E−04 | 1383 | 101723 | 1995 | 780611 | 4045 | 224270 | 0.6 |
| 1E−03 | 1216 | 94634 | 103974 | 120423 | 146861 | 216645 | 1.0 |
| 1E−02 | 7754 | 542450 | 525599 | 470042 | 532701 | 542164 | 1.0 |
| 1E−01 | 105820 | 2454365 | 2360196 | 2583783 | 2180677 | 2157157 | 1.0 |
| | | | | | | 4.8 | Sum |
| | | | | | | 2.00E+04 | $TU_{50}$(100 uL) |
| | | | | | | 2.00E+05 | $TU_{50}$/mL |
| | | | | | | 3.83E+03 | Ratio |

Example 3. Homologous Recombination Constructs

The homologous recombination products are depicted in FIG. 4. Parent Phage indicates the wild type input phage used for recombination. Fusion Protein identifies the protein of interest (POI) used for a fusion partner to HiBiT. HR Donor Plasmid provides the name of the plasmid transformed into the HR host. Vector Backbone provides the name of the vector used to clone the HR region (GENEWIZ provided vector). GENEWIZ clone ID is the unique identifier used by GENEWIZ to track the clone are report the QC data. Cleavage Site indicates which protease cleavage site was used to connect HiBiT and fusion partner. HR Host/Stain indicates the species and strain used in the recombination and isolation infections. The Phage Lot indicates if the phage was fully isolated it would be stored (NA) or a large scale prep was made (Phage Lot #). An incomplete indicated that the a) recombinant was not stable or b) unable to be fully isolated or c) recombination was not attempted.

Example 4. HiBiT Assay Optimization

Samples were added to the microtiter assay well. Each microtiter assay well containing a sample received the components listed in Table 5 according to the HiBiT lytic Kit manufacturer's instructions. The reaction was mixed by nutator for 10 minutes prior to reading on the luminometer. Initial experiments of our transformed HR hosts and HR infection lysate revealed a relatively high (~500 RLU) background signal in media alone.

TABLE 5

| HiBiT Assay Components | | |
|---|---|---|
| Component | Lot# | Vol (uL) |
| HiBiT Lytic Assay Buffer | 0000346748 | 50 |
| LgBT:Large BiT subunit | 0000363377 | 0.5 |
| HB Sub:HiBiT NanoGlo Substrate | 0000364833 | 1 |

Subsequent experiments determined that the elevated background could be attributed to samples containing media. Elevated background levels were not detected in assays using S-M Buffer, water, or phage in S-M buffer. In an effort to identify the source of the high background, several medias were 2-fold serially-diluted in sterile d-water and 100 uL of each assayed as above and reported in Table 6.

TABLE 6

Media Background Signals (RLU)

|  |  | TSB NB3-116A | BHI NB3-115A | Terrific Broth NB3-105D | LB NB3-53A | BPW |
|---|---|---|---|---|---|---|
| Concentration | 1X | 792 | 2505 | 373 | 446 | 1348 |
|  | 0.5X | 625 | 2760 | 330 | 367 | 826 |
|  | 0.25X | 456 | 2626 | 248 | 276 | 475 |
|  | 0.125X | 331 | 2832 | 260 | 280 | 438 |
|  | 0 | 28 | 24 | 25 | 20 | 22 |

Additionally, several media components were dissolved at twice (2×) the recommended concentration in sterile water, serially diluted 2-fold and subjected to the HiBiT Assay as described above (Table 7).

TABLE 7

2X Media Background Signals (RLU)

|  |  | Tryptone (Fisher) | Tryptone (Sigma) | yeast extract | LB | TSB | BHI |
|---|---|---|---|---|---|---|---|
| Concentration | 2X | 566 | 3288 | 2042 | 971 | 1301 | 5362 |
|  | 1X | 411 | 3474 | 2136 | 907 | 1188 | 6104 |
|  | 0.5X | 274 | 2578 | 1648 | 726 | 862 | 5703 |
|  | 0.25X | 234 | 2284 | 1750 | 968 | 801 | 6151 |
|  | 0 | 18 | 23 | 27 | 25 | 33 | 30 |

The results indicated that all media tested had high background and both BHI and Tryptone (Sigma) had a very high background (2000-6000 RLUs). The signal appears saturating even when the media/component was diluted 8-fold. An experiment was performed to discern which component of the Lytic kit assay in conjunction with the BHI is the cause of the very high RLUs in the absence of HiBiT. Table 8 shows the LgBiT component is interacting with the BHI to give the high RLU background in the presence of furimazine substrate. Also noted here is the true background of LgBiT and furimazine in buffer alone, which was also high at 110-180 RLUs.

TABLE 8

Media Component Background Signal (RLU)

|  |  | HiBit Buffer | NanoGlo Buffer |
|---|---|---|---|
| COMPONENTS | BHI | 6 | 11 |
|  | BHI + LgBT | 4 | 21 |
|  | BHI + LgBT + HB sub | 13778 | 6860 |
|  | BHI + LgBT + NG sub | 9941 | 12143 |
|  | BHI + HB Sub | 27 | 24 |
|  | BHI + NG Sub | 31 | 23 |
|  | LgBT + HB sub | 180 | 113 |

In order to reduce the high background associated with just LgBiT, media, and substrate, the concentration of LgBiT was lowered 5-10 fold (Table 9).

Table 9 shows an approximate 6-fold drop in background signal when LgBiT was reduced to 0.05 μL/reaction versus the manufacturer recommended 0.5 μL/reaction. For all subsequent HiBiT assays, the LgBiT component was reduced to at least 0.1 μL/reaction to mitigate media-associated background RLUs.

TABLE 9

LgBiT and Media Background Signal

|  |  | RLU |
|---|---|---|
| LgBT:Large BiT subunit (0.05 uL/reaction) | BHI | 403 |
| [LOT# 0000363377] | LB | 62 |
| HB Sub:HiBiT NanoGlo Substrate | TSB | 132 |
| [LOT# 0000364833] | TB | 65 |
| HiBiT Lytic Assay Buffer | TMS | 15 |
| [LOT#0000346758] | PBST | 18 |
| Media listed: 100 uL/reaction | dH2O | 11 |

Example 5. Recombinant Phage Generation

Recombinant phages expressing either soluble HiBiT or a HiBiT tag fused to a structural protein were created by standard infection of host bacteria containing the homologous recombination donor plasmid. The homologous recombination (HR) plasmid was transformed into the preferred host bacteria by electroporation. Transformants containing the plasmid were selected by growth on antibiotic selective plates. The host was grown under selective pressure to early-mid log phase and HiBiT activity was measured in the culture.

Bacterial cells surviving selection and showing HiBiT activity were then uses as the host for the HR infection. Log cells were diluted to approximately 1.0E+07 cells/mL in media with antibiotic. Native/wild-type phage were added at a MOI of about 0.05-1.0 and the infection was incubated for 3-5 hours at a preferred temperature with shaking. Following incubation, any remaining bacterial host cells and cell debris were pelleted by centrifugation at 5000×g for 5 minutes. The lysate was collected and filtered through a 0.45 micron filter to eliminate any remaining host cells.

Phage lysates were then prepared for an endpoint dilution and plaque assays to determine the estimate recombinant/plaque titers. The phage lysate was buffer exchanges to remove all unincorporated/host-derived HiBiT by passing the lysate through a 100,000 Dalton molecular weight cut off spin filter with additional 4 volumes of wash buffer. Resulting phage were suspended in 0.5 mL buffer/media and eight 10-fold dilutions were performed in media.

Phage titers were then determined by tittering the HR lysate for HiBiT recombinants using a $TU_{50}$ Assay (Transducing Units 50%). Wells showing no HiBiT activity above the background (phage and media alone) were scored as negative and wells with 3× background RLUs were scored as positive. Calculation of $TU_{50}$ titer was based on Reed-Muench method. The same serial dilutions were tittered by plaque assay. The $TU_{50}$ titer was compared to the plaque assay titer to determine the recombinant/total phage titer ratio.

If the recombinant/total phage titer ratio was less than 1/30, limiting dilution enrichment was performed until the ratio was at or above 1/30. Limiting dilution enrichment was performed by dilution of the lysate to include 1-10 Transducing Units in 5 mL media. Native host bacteria were then added to the diluted phage at a low MOI and distributed amongst wells of a 96-well culture plate. Phage infection was incubated 3-16 hours at 25-37° C. 10% of each well was subject to HiBiT Assay and top positive wells underwent the phage titer assays described above. Sequential limiting dilution enrichments were performed until the recombinant/total phage titer ratio was less than 1/30.

Plaque isolation of recombinant phage is performed once a favorable recombinant/total titer ratio was achieved. Individual plaques were isolated and screened for HiBiT activity. Positive plaques are passaged at least 3 times to purity. Fully isolated recombinants were produced by large scale infection and purified by cesium or sucrose gradient centrifugation.

Example 6. Phage Concentration Optimization of TSP1.sHiBiT (TSP1 with Soluble Unfused Hibit Monomer)

*Salmonella typhimurium* (ATCC 19585) were cultured for 16-18 hours in TSB at 37° C. Cells were diluted to 10, 20, 50, 100, 1000, 10000, and 100,000 CFU/mL. 100 μL of the diluted cells were pipetted to give 1, 2, 5, 10, 100, 1000, and 10000 CFU/well in a white 96-well plate. 10 μL of TSP1.sHiBit phage at $1.2 \times 10^4$ to $10^8$ PFU/mL was added to each well (TABLE 10).

TABLE 10

HiBiT Phage Assay Plate Layout

| Phage/mL | $10^4$ P/mL | $10^5$ P/mL | $10^6$ P/mL | $10^7$ P/mL | $10^8$ P/mL |
|---|---|---|---|---|---|
| A | 0 | 0 | 0 | 0 | 0 |
| B | 1 | 1 | 1 | 1 | 1 |
| C | 2 | 2 | 2 | 2 | 2 |
| D | 5 | 5 | 5 | 5 | 5 |
| E | 10 | 10 | 10 | 10 | 10 |
| F | 100 | 100 | 100 | 100 | 100 |
| G | 1000 | 1000 | 1000 | 1000 | 1000 |
| H | 10000 | 10000 | 10000 | 10000 | 10000 |

Figure 5:
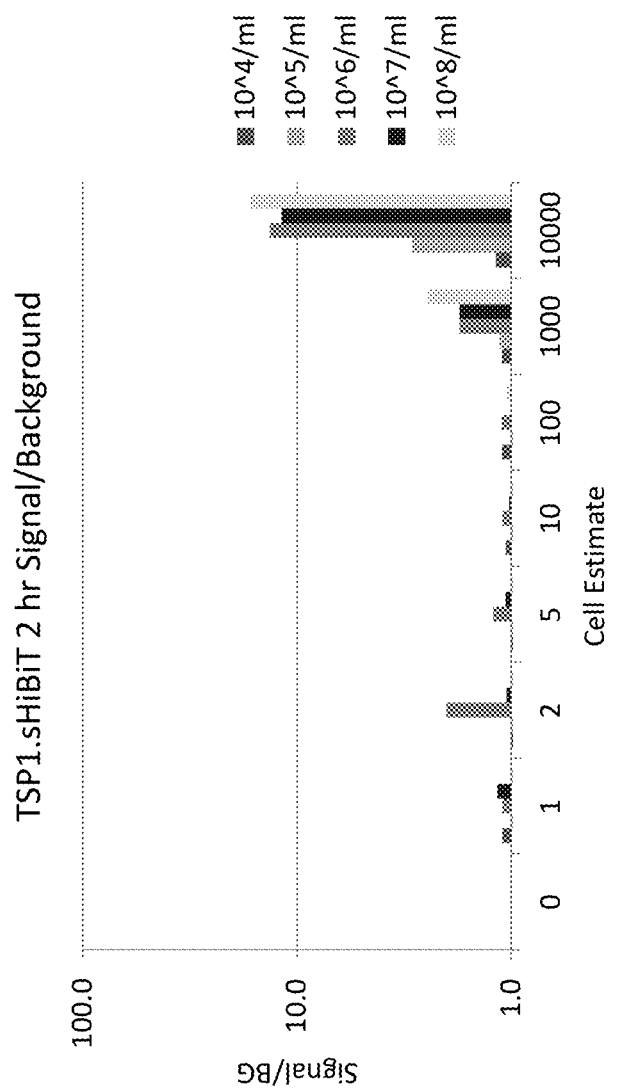
FIG. 5 illustrates optimization of TSP1.sHiBiT phage concentration for detection of *Salmonella typhimurium* with a 2 hour incubation in accordance with an embodiment of the disclosure.
Figure 6:
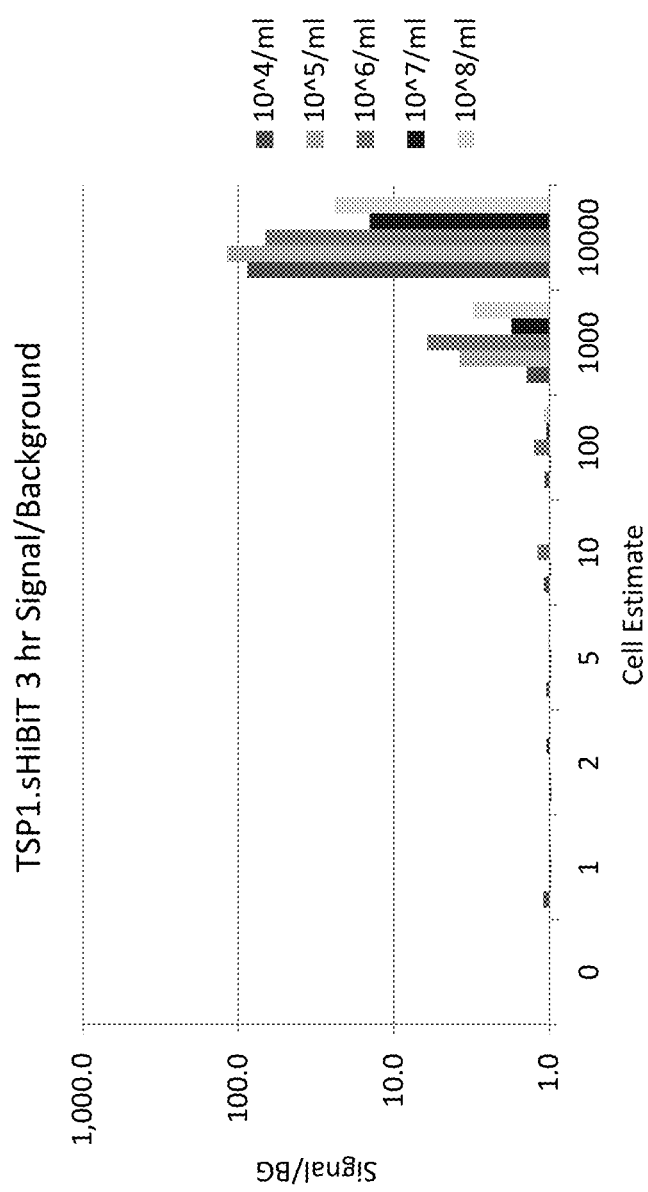
FIG. 6 illustrates optimization of TSP1.sHiBiT phage concentration for detection of *Salmonella typhimurium* with a 3 hour incubation in accordance with an embodiment of the disclosure.

The plate was incubated at 37° C. for 2 hours or 3 hours. 50 μL of master mix (50 μL Assay buffer (NanoGlo HiBiT Buffer), 1 μL NanoGlo HiBit Substrate, and 0.1 μL LgBiT protein) was added to each well, incubated at room temperature on the nutator, and read in the GloMax/Navigator for 1 second. Signal/Background values for the 2 hour incubation are shown in FIG. 5. Signal/Background values for the 3 hour incubation are shown in FIG. 6. The 3 hour incubation time had an improved signal/background ratio.

Example 7. Phage Concentration Optimization of TSP12.sHiBiT, TSP12 Expressing Soluble HiBiT Peptide

Figure 7:
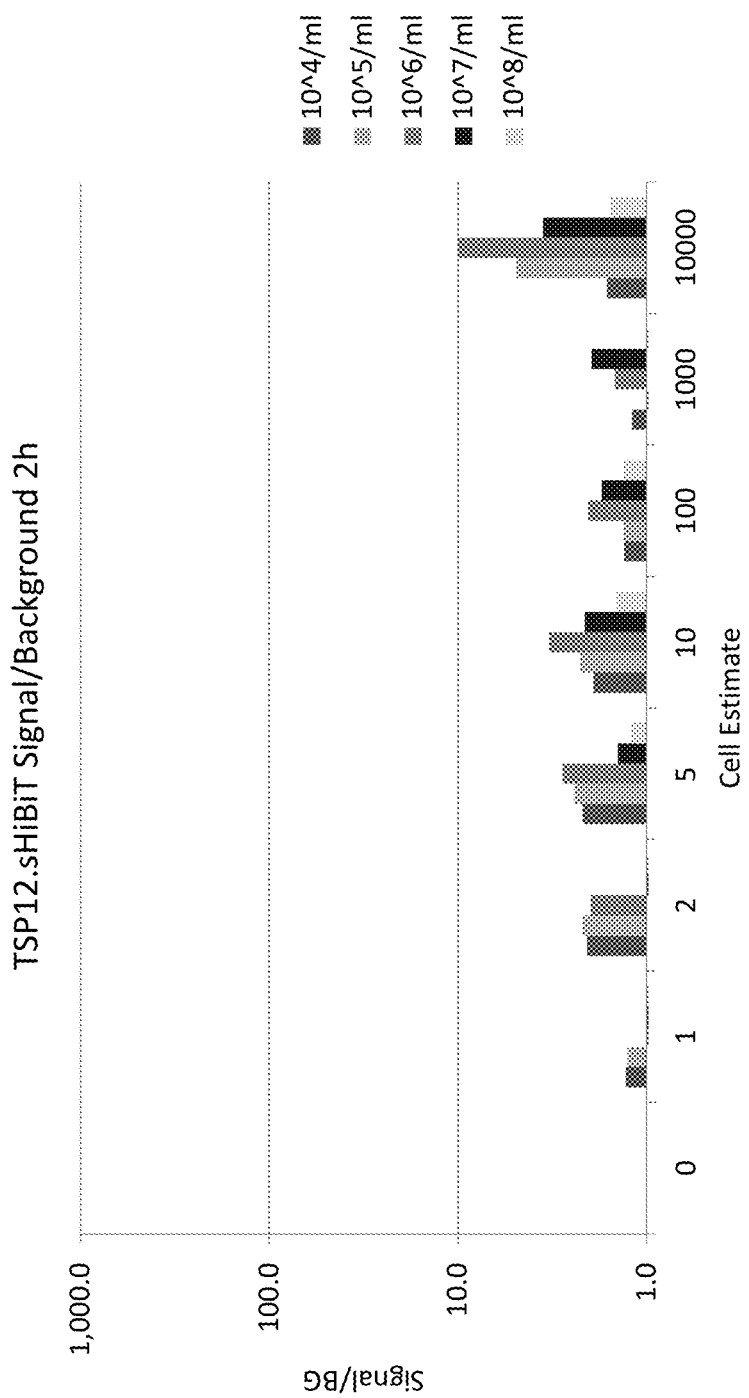
FIG. 7 illustrates optimization of TSP12.sHiBiT phage concentration for detection of *Salmonella bongori* with a 2 hour incubation in accordance with an embodiment of the disclosure.
Figure 8:
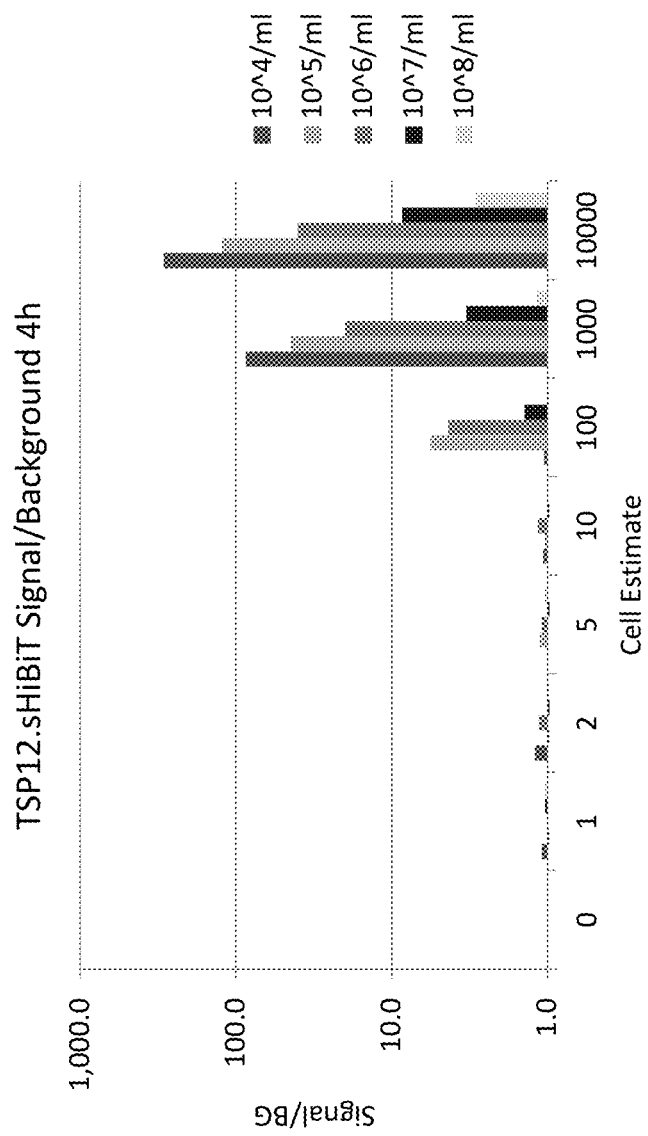
FIG. 8 illustrates optimization of TSP12.sHiBiT phage concentration for detection of *Salmonella bongori* with a 4 hour incubation in accordance with an embodiment of the disclosure.

*Salmonella bongori* (ATCC 43975) were cultured for 16-18 hours in TSB at 37° C. Cells were diluted to 10, 20, 50, 100, 1000, 10000, and 100,000 CFU/ml. 100 μL of the diluted cells were pipetted to give 1, 2, 5, 10, 100, 1000, and 10000 CFU/well in a white 96-well plate. 10 μL of TSP12.sHiBit phage at $1.2 \times 10^4$ to $10^8$ PFU/mL was added to each well (TABLE 10). The plate was incubated at 37° C. for 2 hours or 4 hours. 50 μL of master mix (50 μL Assay buffer (NanoGlo HiBiT Buffer), 1 μL NanoGlo HiBit Substrate, and 0.1 μL LgBiT protein) was added to each well, incubated at room temperature on the nutator, and read in the GloMax/Navigator for 1 second. Signal/Background values for the 4 hour incubation are shown in FIG. 7. Signal/Background values for the 3 hour incubation are shown in FIG. 8. The 4 hour incubation time had an improved signal/background ratio.

Example 8. Phage Concentration Optimization of TSP12.HiBiT-PS-Soc

Figure 9:
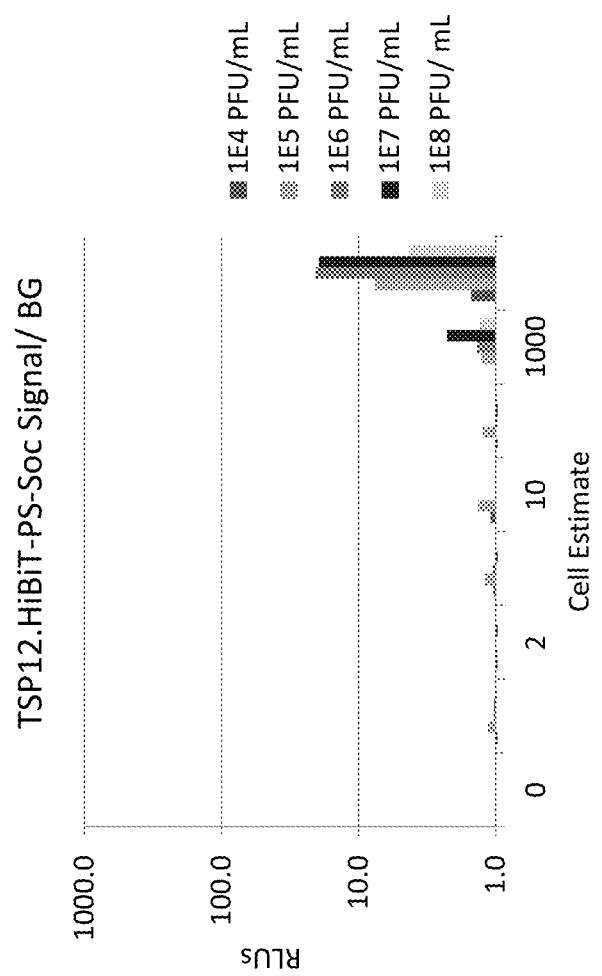
FIG. 9 illustrates optimization of TSP12.HiBiT-PS-Soc phage concentration for detection of *Salmonella bongori* with a 2 hour incubation in accordance with an embodiment of the disclosure.

*Salmonella bongori* (ATCC 43975) were cultured for 16-18 hours in TSB at 37° C. Cells were diluted to 10, 20, 50, 100, 1000, 10000, and 100,000 CFU/ml. 100 μL of the diluted cells were pipetted to give 1, 2, 5, 10, 100, 1000, and 10000 CFU/well in a white 96-well plate. 10 μL of TSP12.HiBit-PS-Soc phage at $1.2 \times 10^4$ to $10^8$ PFU/mL was added to each well (TABLE 10). The plate was incubated at 37° C. for 2 hours. 50 μL of master mix (50 μL Assay buffer (NanoGlo HiBiT Buffer), 1 μL NanoGlo HiBit Substrate, and 0.1 μL LgBiT protein) was added to each well, incubated at room temperature on the nutator, and read in the GloMax/Navigator for 1 second. Signal/Background values for the 2 hour incubation are shown in FIG. 9.

Example 9. Level of Detection of TSP12.HiBiT-PS-Soc

Figure 10:
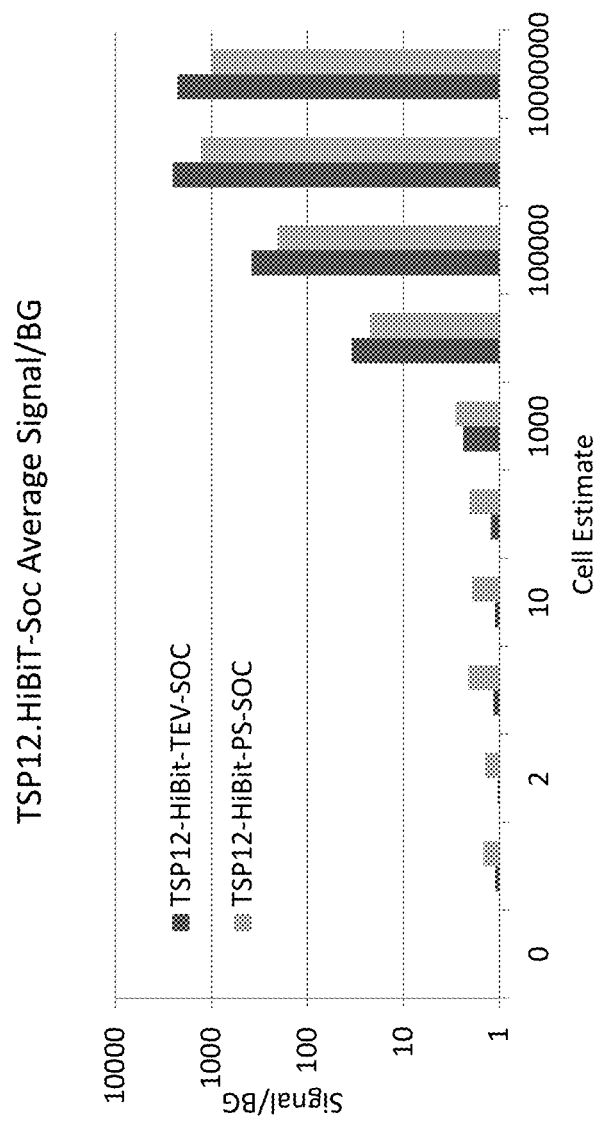
FIG. 10 illustrates the level of detection of TSP12.HiBiT-PS-Soc phage for *Salmonella bongori* with a 2 hour incubation in accordance with an embodiment of the disclosure.

*Salmonella bongori* (ATCC 43975) were cultured for 16-18 hours in TSB at 37° C. Cells were diluted to 10, 20, 50, 100, 1000, 10000, and 100,000 CFU/ml. 100 μL of the diluted cells were pipetted to give 1, 2, 5, 10, 100, 1000, and 10000 CFU/well in a white 96-well plate. 10 μL of TSP12-HTS or TSP12-HPS phage at $1.2 \times 10^7$ PFU/mL was added to each well (TABLE 10). The plate was incubated at 37° C. for 2 hours. 50 μL of master mix (50 μL Assay buffer (NanoGlo HiBiT Buffer), 1 μL NanoGlo HiBit Substrate, and 0.1 μL LgBiT protein) was added to each well, incubated for 10 minutes at room temperature on the nutator, and read in the GloMax/Navigator for 1 second. Signal/Background values are shown in FIG. 10.

We claim:

1. A method for detecting a particular bacteria of interest in a sample comprising:
   incubating the sample with a recombinant indicator bacteriophage comprising an indicator gene, wherein the indicator gene encodes a first subunit of an indicator protein, thereby producing an amount of progeny phage expressing the first subunit;
   lysing the amount of progeny phage;
   incubating the lysed progeny phage in presence of a detection reagent, wherein the detection reagent comprises a second subunit of an indicator protein, thereby allowing the first subunit and second subunit to reconstitute to form an indicator protein complex; and
   detecting the indicator protein complex, wherein positive detection of the indicator protein complex indicates that the particular bacteria of interest is present in the sample.

2. The method of claim 1, wherein the sample is a food, environmental, water, or commercial sample.

3. The method of claim 1, wherein the method detects as few as 10, 9, 8, 7, 6, 5, 4, 3, 2, or a single bacterium in a sample of a standard size for food safety industry.

4. The method of claim 2, wherein the food sample comprises meat, fish, vegetables, eggs, dairy products, dried food products, or powdered infant formula.

5. The method of claim 1, wherein the sample is first incubated in conditions favoring growth for an enrichment period of less than 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, or 2 hours.

6. The method of claim 1, wherein total time to results is less than 26 hours, 25 hours, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours 8 hours, 7 hours, 6 hours, 5 hours, 4 hours, 3 hours, or 2 hours.

7. The method of claim 1, wherein ratio of signal to background generated by detecting the indicator protein complex is at least 2.0 or at least 2.5.

* * * * *